United States Patent
Burbank et al.

(10) Patent No.: US 6,679,851 B2
(45) Date of Patent: Jan. 20, 2004

(54) TISSUE ACCESSING AND ANCHORING DEVICE AND METHOD

(75) Inventors: Fred H. Burbank, Laguna Niguel, CA (US); Paul Lubock, Laguna Niguel, CA (US); John Wardle, San Clemente, CA (US); Frank Louw, Carlsbad, CA (US); Richard L. Quick, Mission Viejo, CA (US)

(73) Assignee: SenoRx, Inc., Aliso Viejo, CA (US)

( * ) Notice: Subject to any disclaimer, the term of this patent is extended or adjusted under 35 U.S.C. 154(b) by 0 days.

(21) Appl. No.: 09/880,218

(22) Filed: Jun. 12, 2001

(65) Prior Publication Data

US 2002/0058884 A1 May 16, 2002

Related U.S. Application Data

(63) Continuation-in-part of application No. 09/146,185, filed on Sep. 1, 1998, now Pat. No. 6,540,693, and a continuation-in-part of application No. 09/159,467, filed on Sep. 23, 1998, now Pat. No. 6,261,241, and a continuation-in-part of application No. 09/356,187, filed on Jul. 16, 1999, now Pat. No. 6,312,429, and a continuation-in-part of application No. 09/477,255, filed on Jan. 4, 2000, now Pat. No. 6,471,700, and a continuation-in-part of application No. 09/727,112, filed on Nov. 29, 2000, now Pat. No. 6,638,234.

(51) Int. Cl.⁷ .............................................. A61B 10/00
(52) U.S. Cl. ..................................................... 600/564
(58) Field of Search .................................. 600/562–579

(56) References Cited

U.S. PATENT DOCUMENTS 2,032,860 A   3/1936   Wappler et al.

(List continued on next page.)

FOREIGN PATENT DOCUMENTS

| DE | 12 25 813 | 9/1966 |
|---|---|---|
| DE | 19528440 A1 | 8/1995 |
| EP | 146699 | 9/1984 |
| EP | 0255123 | 2/1988 |
| EP | 0292936 | 11/1988 |
| EP | 0472368 A2 | 8/1991 |
| EP | 0481685 A1 | 10/1991 |
| EP | 0 601 709 A2 | 6/1994 |
| EP | 0 667 126 A1 | 8/1995 |

(List continued on next page.)

OTHER PUBLICATIONS

J. S. Armstrong et al. "Differential marking of excision planes in screened breast lesions by organically coloured gelantins [see comments]" *Journal of Clinical Pathology* (Jul. 1990) 43(7):604–607, XP000971447 abstract; tables 1 and 2.

(List continued on next page.)

*Primary Examiner*—Eric F. Winakur
*Assistant Examiner*—David J. McCrosky
(74) *Attorney, Agent, or Firm*—Edward J. Lynch; Duane Morris LLP

(57) ABSTRACT

The invention provides systems, methods and a node accessing and anchoring device, comprising an elongated shaft, a tissue cutting member, at least one anchoring element extending from a position at or near the distal end of the shaft; and a radiation detector. The radiation detector is effective to locate and identify sentinel lymph nodes following injection of radioactive material into a primary lesion site within a patient. The tissue cutting member, which may be activated with radio frequency energy, is effective to allow access of the elongated shaft to a sentinel lymph node. The anchoring elements are effective to anchor the device to or adjacent a sentinel lymph node accessed by the device. Anchoring elements may assume radially, longitudinally, or mixed radially and longitudinally curved or coiled configurations when deployed.

26 Claims, 26 Drawing Sheets

U.S. PATENT DOCUMENTS

| | | | |
|---|---|---|---|
| 2,192,270 A | 3/1940 | McGowan | |
| 3,341,417 A | 9/1967 | Sinaiko | |
| 3,805,791 A | 4/1974 | Seuberth et al. | |
| 3,818,894 A | 6/1974 | Wichterle et al. | |
| 3,823,212 A | 7/1974 | Chvapil | |
| 3,955,578 A | 5/1976 | Chamness et al. | |
| 4,007,732 A | 2/1977 | Kvavle et al. | 128/2 |
| 4,172,449 A | 10/1979 | LeRoy et al. | |
| 4,197,846 A | 4/1980 | Bucalo | |
| 4,202,338 A | 5/1980 | Bitrolf | |
| 4,243,048 A | 1/1981 | Griffin | |
| 4,276,885 A | 7/1981 | Tickner et al. | |
| 4,294,241 A | 10/1981 | Miyata | |
| 4,294,254 A | 10/1981 | Chamness | |
| 4,311,143 A | 1/1982 | Komiya | |
| 4,331,654 A | 5/1982 | Morris | |
| 4,362,160 A | 12/1982 | Hiltebrandt | 128/303.15 |
| 4,425,908 A | 1/1984 | Simon | |
| 4,503,855 A | 3/1985 | Maslanka | |
| 4,545,367 A | 10/1985 | Tucci | |
| 4,565,200 A | 1/1986 | Cosman | 128/642 |
| 4,576,162 A | 3/1986 | McCorkle | |
| 4,592,356 A | 6/1986 | Gutierrez | |
| 4,616,656 A | 10/1986 | Nicholson et al. | |
| 4,638,802 A | 1/1987 | Okada | |
| 4,643,187 A | 2/1987 | Okada | |
| 4,647,480 A | 3/1987 | Ahmed | |
| 4,682,606 A | 7/1987 | DeCaprio | 600/567 |
| 4,693,237 A | 9/1987 | Hoffman et al. | |
| 4,718,419 A | 1/1988 | Okada | |
| 4,724,836 A | 2/1988 | Okada | |
| 4,774,948 A | 10/1988 | Markham | |
| 4,813,062 A | 3/1989 | Gilpatrick | |
| 4,847,049 A | 7/1989 | Yamamoto | |
| 4,863,470 A | 9/1989 | Carter | |
| 4,909,250 A | 3/1990 | Smith | 606/117 |
| 4,931,059 A | 6/1990 | Markham | 606/185 |
| 4,959,547 A | 9/1990 | Carroll et al. | |
| 4,966,583 A | 10/1990 | Debbas | 604/98 |
| 5,007,908 A | 4/1991 | Rydell | |
| 5,024,617 A | 6/1991 | Karpiel | |
| 5,035,696 A | 7/1991 | Rydell | |
| 5,047,027 A | 9/1991 | Kozak et al. | |
| 5,059,197 A | 10/1991 | Urie et al. | |
| 5,064,424 A | 11/1991 | Bitrolf | |
| 5,066,295 A | 11/1991 | Kozak et al. | |
| 5,078,716 A | 1/1992 | Doll | |
| 5,080,660 A | 1/1992 | Buelna | |
| RE33,925 E | 5/1992 | Bales et al. | 606/48 |
| 5,111,828 A | 5/1992 | Kornberg et al. | 128/754 |
| 5,133,359 A | 7/1992 | Kedem | |
| RE34,056 E | 9/1992 | Lindgren et al. | 128/754 |
| 5,147,307 A | 9/1992 | Gluck | |
| 5,151,598 A | 9/1992 | Denen | |
| 5,158,084 A | 10/1992 | Ghiatas | 128/657 |
| 5,158,561 A | 10/1992 | Rydell et al. | |
| 5,163,938 A | 11/1992 | Kambara et al. | |
| 5,196,007 A | 3/1993 | Ellman et al. | |
| 5,201,732 A | 4/1993 | Parins et al. | |
| 5,201,741 A | 4/1993 | Dulebohn | |
| 5,207,686 A | 5/1993 | Dolgin | |
| 5,217,458 A | 6/1993 | Parins | 600/564 |
| 5,221,269 A | 6/1993 | Miller et al. | |
| 5,224,488 A | 7/1993 | Neuffer | |
| 5,234,426 A | 8/1993 | Rank et al. | |
| 5,236,410 A | 8/1993 | Granov et al. | |
| 5,281,218 A | 1/1994 | Imran | 606/21 |
| 5,281,408 A | 1/1994 | Unger | |
| 5,282,781 A | 2/1994 | Liprie | |
| 5,312,400 A | 5/1994 | Bales et al. | |
| 5,318,564 A | 6/1994 | Eggers | |
| 5,323,768 A | 6/1994 | Saito et al. | |
| 5,324,288 A | 6/1994 | Billings et al. | |
| 5,334,381 A | 8/1994 | Unger | |
| 5,335,671 A | 8/1994 | Clement | |
| 5,344,420 A | 9/1994 | Hilal et al. | |
| 5,368,030 A | 11/1994 | Zinreich et al. | |
| 5,376,094 A | 12/1994 | Kline | |
| 5,380,321 A | 1/1995 | Yoon | |
| 5,395,312 A | 3/1995 | Desai | |
| 5,395,319 A | 3/1995 | Hirsch et al. | 604/60 |
| 5,409,004 A | 4/1995 | Sloan | |
| 5,415,656 A | 5/1995 | Tihon et al. | |
| 5,417,697 A | 5/1995 | Wilk et al. | |
| 5,422,730 A | 6/1995 | Barlow et al. | |
| 5,423,814 A | 6/1995 | Zhu et al. | |
| 5,431,649 A | 7/1995 | Mulier et al. | 606/41 |
| 5,433,204 A | 7/1995 | Olson | |
| 5,437,665 A | 8/1995 | Munro | 606/47 |
| 5,441,503 A | 8/1995 | Considine et al. | |
| 5,449,382 A | 9/1995 | Dayton | |
| 5,462,553 A | 10/1995 | Dolgin | |
| 5,470,308 A | 11/1995 | Edwards et al. | 604/22 |
| 5,477,862 A | 12/1995 | Haga | |
| 5,484,436 A | 1/1996 | Eggers et al. | |
| 5,487,385 A | 1/1996 | Avitall | 600/374 |
| 5,488,958 A | 2/1996 | Topel et al. | 600/567 |
| 5,494,030 A | 2/1996 | Swartz et al. | |
| 5,501,654 A | 3/1996 | Failla et al. | |
| 5,526,822 A | 6/1996 | Burbank et al. | 128/754 |
| 5,538,010 A | 7/1996 | Darr et al. | |
| 5,542,948 A | 8/1996 | Weavers et al. | |
| 5,549,560 A | 8/1996 | Van de Wijdeven | |
| 5,607,389 A | 3/1997 | Edwards et al. | |
| 5,611,803 A | 3/1997 | Heaven et al. | |
| 5,636,255 A | 6/1997 | Ellis | |
| 5,643,246 A | 7/1997 | Leeb et al. | |
| 5,643,282 A | 7/1997 | Kieturakis | |
| 5,646,146 A | 7/1997 | Faarup et al. | |
| 5,649,547 A | 7/1997 | Ritchart et al. | 128/754 |
| 5,653,718 A | 8/1997 | Yoon | |
| 5,665,085 A | 9/1997 | Nardella | |
| 5,674,184 A | 10/1997 | Hassler, Jr. | |
| 5,676,925 A | 10/1997 | Klaveness et al. | |
| 5,683,384 A | 11/1997 | Gough et al. | |
| 5,687,739 A | 11/1997 | McPherson et al. | 128/754 |
| 5,688,490 A | 11/1997 | Tournier et al. | |
| 5,700,273 A | 12/1997 | Buelna et al. | |
| 5,715,825 A | 2/1998 | Crowley | 128/602.06 |
| 5,720,763 A | 2/1998 | Tovey | |
| 5,732,704 A | 3/1998 | Orahood et al. | |
| 5,735,847 A | 4/1998 | Gough et al. | |
| 5,741,225 A | 4/1998 | Lax et al. | 604/22 |
| 5,749,887 A | 5/1998 | Heske et al. | 606/185 |
| 5,752,972 A | 5/1998 | Hoogeboom | |
| 5,755,697 A | 5/1998 | Jones et al. | 604/174 |
| 5,766,163 A | 6/1998 | Mueller et al. | |
| 5,769,086 A | 6/1998 | Ritchart et al. | |
| 5,772,660 A | 6/1998 | Young et al. | |
| 5,775,333 A | 7/1998 | Burbank et al. | 128/754 |
| 5,782,764 A | 7/1998 | Werne | 600/411 |
| 5,782,775 A | 7/1998 | Milliman et al. | 600/567 |
| 5,794,626 A | 8/1998 | Kieturakis | 600/567 |
| 5,795,308 A | 8/1998 | Russin | |
| 5,797,907 A | 8/1998 | Clement | 606/49 |
| 5,800,378 A | 9/1998 | Edwards et al. | 602/22 |
| 5,800,445 A | 9/1998 | Ratcliff et al. | 606/116 |
| 5,810,806 A | 9/1998 | Ritchart et al. | |
| 5,846,513 A | 12/1998 | Carroll et al. | |
| 5,853,366 A | 12/1998 | Dowlatshahi | 600/434 |
| 5,857,463 A | 1/1999 | Thurston et al. | |

| | | |
|---|---|---|
| 5,868,740 A | 2/1999 | LeVeen et al. |
| 5,876,340 A | 3/1999 | Tu et al. |
| 5,879,357 A | 3/1999 | Heaton et al. ............... 606/116 |
| 5,902,272 A | 5/1999 | Eggers et al. |
| 5,902,310 A | 5/1999 | Foerster et al. |
| 5,913,857 A | 6/1999 | Ritchart et al. |
| 5,916,167 A | 6/1999 | Kramer et al. |
| 5,925,044 A | 7/1999 | Hofmann et al. |
| 5,928,150 A | 7/1999 | Call |
| 5,928,164 A | 7/1999 | Burbank et al. |
| 5,947,964 A | 9/1999 | Eggers et al. |
| 5,954,670 A | 9/1999 | Baker |
| 5,961,458 A | 10/1999 | Carroll |
| 5,964,716 A | 10/1999 | Gregoire et al. ............ 600/564 |
| 5,972,002 A | 10/1999 | Bark et al. .................. 606/140 |
| 5,984,919 A | 11/1999 | Hilal et al. .................... 606/45 |
| 5,989,265 A | 11/1999 | De La Joliniere et al. .. 606/116 |
| 6,004,269 A | 12/1999 | Crowley et al. ............ 600/439 |
| 6,050,955 A | 4/2000 | Bryan et al. |
| 6,056,700 A | 5/2000 | Burney et al. ............... 606/167 |
| 6,063,082 A | 5/2000 | DeVore et al. ................ 606/45 |
| 6,142,955 A | 11/2000 | Farascioni et al. |
| 6,161,034 A | 12/2000 | Burbank et al. ............ 600/431 |
| 6,234,177 B1 | 5/2001 | Barsch |
| 2001/0002250 A1 | 5/2001 | Burbank et al. |

FOREIGN PATENT DOCUMENTS

| | | |
|---|---|---|
| EP | 0667126 A1 | 8/1995 |
| EP | 0 797 957 A1 | 1/1997 |
| EP | 0 769 281 A2 | 4/1997 |
| EP | 0 983 749 | 3/2000 |
| GB | 2311468 A | 2/1997 |
| WO | 93/14712 | 5/1993 |
| WO | 93 13718 | 7/1993 |
| WO | PCT/GB94/01536 | 7/1994 |
| WO | PCT/GB94/01537 | 7/1994 |
| WO | 94 27670 | 12/1994 |
| WO | 95/02370 | 1/1995 |
| WO | 95/02371 | 1/1995 |
| WO | 95 03843 | 2/1995 |
| WO | 95 10317 | 4/1995 |
| WO | 96/08208 A1 | 3/1996 |
| WO | 97 29702 | 8/1997 |
| WO | 98 06346 | 2/1998 |
| WO | 98 08441 | 3/1998 |
| WO | 98 24372 | 6/1998 |
| WO | 99/30764 | 6/1999 |
| WO | 99 44506 | 9/1999 |
| WO | 99/44506 | 9/1999 |
| WO | WO 00 12009 | 3/2000 |
| WO | 00 16697 | 3/2000 |
| WO | WO 01/05320 A1 | 1/2001 |
| WO | WO 01 49184 | 7/2001 |

OTHER PUBLICATIONS

Blackwell Science Ltd., "The Loop Electrode: New Device for US–Guided Interstitial Tissue Ablation Using Radio Frequency Electrosurgery—A n Animal Study" 1996 *Min Incas Ther & Allied Technol* 5: 511–516.

V. Fucci et al. "Large Bowel Transit Times Using Radiopaque Markers in Normal Cats", *J. of Am. Animal Hospital Assn.*, Nov.–Dec. 1995 31 (6) 473–7.

N. E. Schindlbeck et al., "Measurement of Colon Transit Time", *J. of Gastroenterology*, No. 28, pp. 399–404, 1990.

English Translation of German Application DE 195 28 440 A1, published Aug. 2, 1995.

International Search Report for PCT/US99/21416 mailed May 19, 2000.

International Search Report for PCT/US01/00543, mailed Jul. 19, 2001.

Written Opinion mailed Jul. 18, 2000, PCT Rule 66, for International Application PCT/US/9921416.

International Search Report for PCT/US01/44265, mailed Sep. 23, 2002.

International Search Report from PCT/US99/04471, mailed Jun. 14, 1999.

F. Burbank, M.D., Sterotactic Breast Biopsy: Its History, Its Present, and Its Future, *The American Surgeon*, Feb. 1996, vol. 62, pp. 128–150.

Laura Liberman, MD, et al., *Sentinel Lymph Node Biopsy after Percutaneous Diagnosis of Nonpalpable Breast Cancer*, Radiology, vol. 211. Jun. 1999, pp. 835–844.

Timothy J. Micklos, Percutaneous Biopsy Techniques, *Manual of Oncologic Thrapeutics*, (1989/1990), pp. 39–42.

Mark S. Pack, M.D. Robert S. Thomas, M.D., "*Axillary Lymph Node Dissection: Does It Have a Role In Primary Breast Cancer?*", The American Surgeon, Feb. 1996, vol. 62, pp. 159–161.

Whitman et al., Coaxial Core Needle Biopsy Under Mammographic Guidance: Indications and Applications, AJR. 171, Jul. 1998, pp. 67–70.

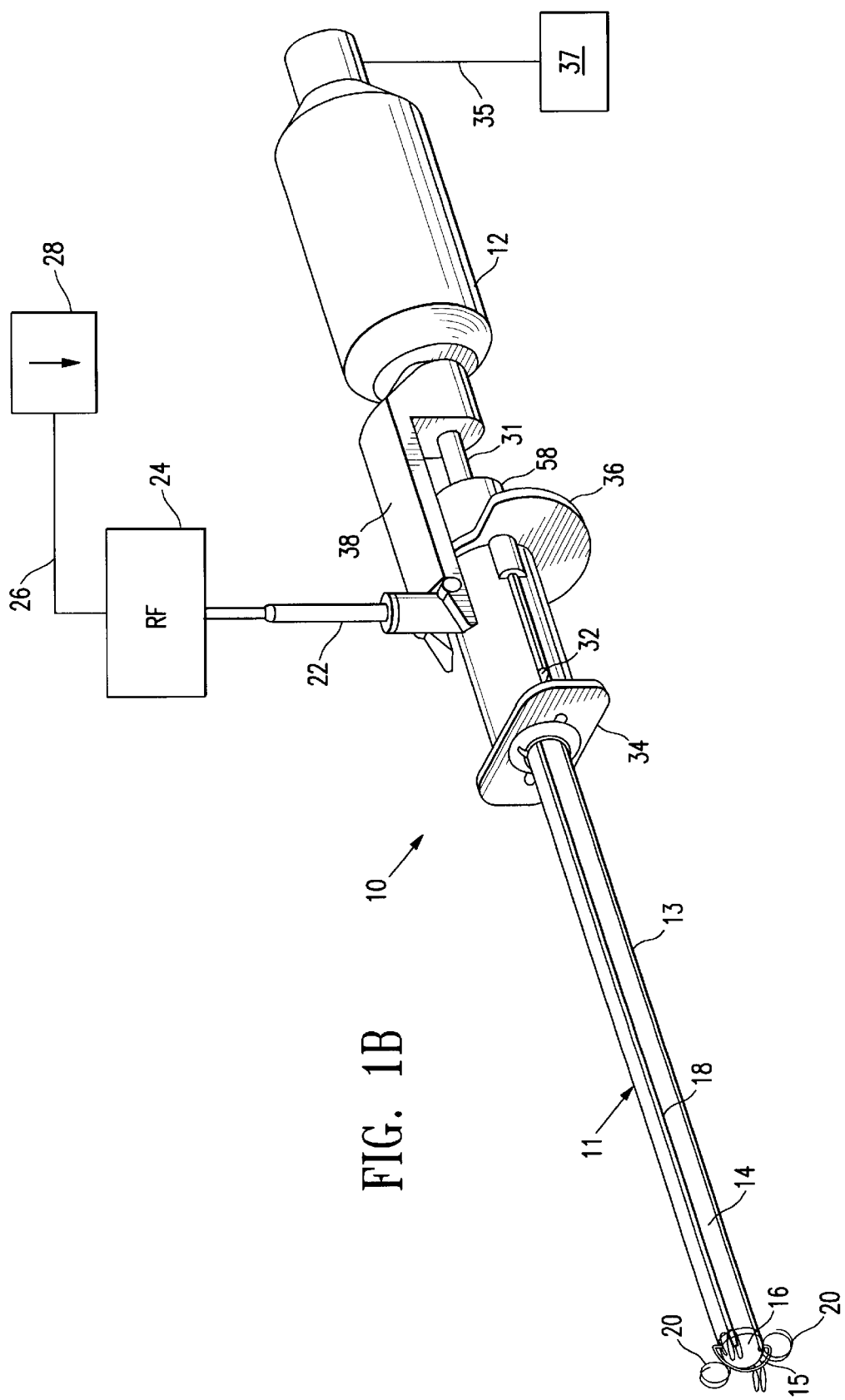

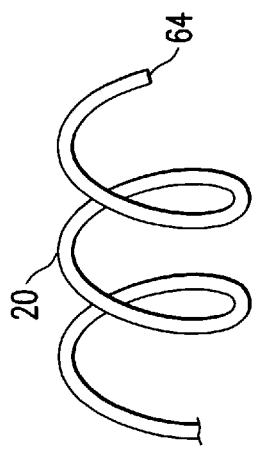
FIG. 14A
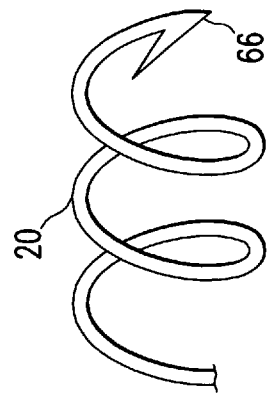
FIG. 14B
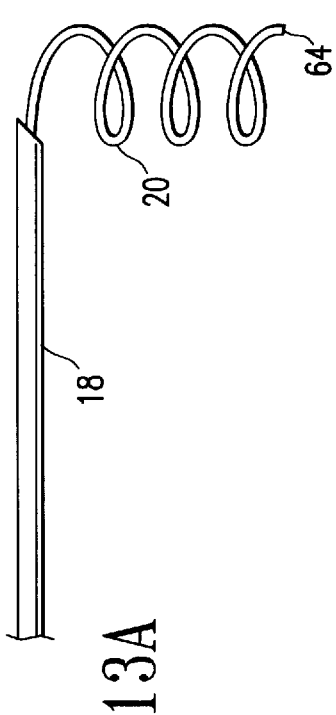
FIG. 13A
FIG. 13B
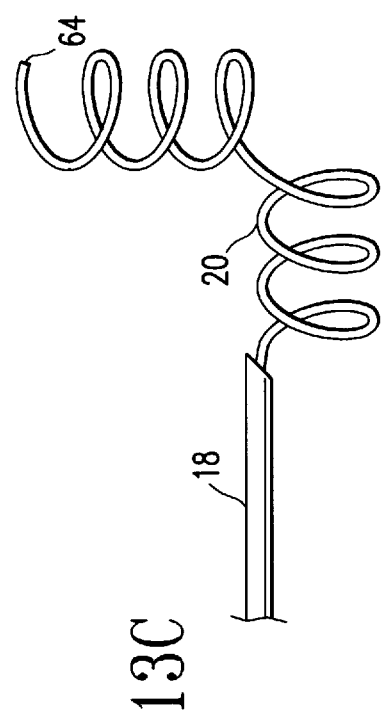
FIG. 13C

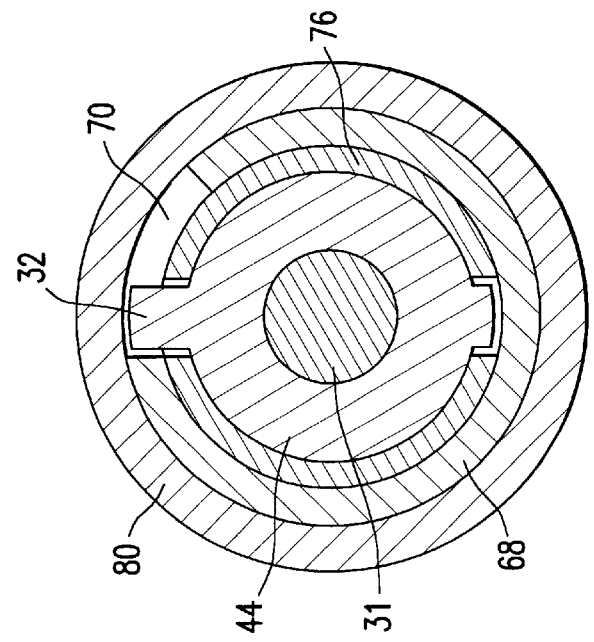
FIG. 15D
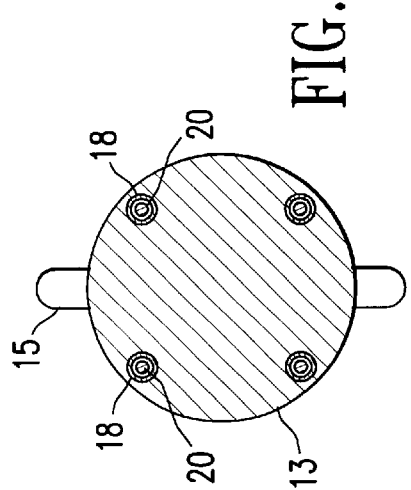
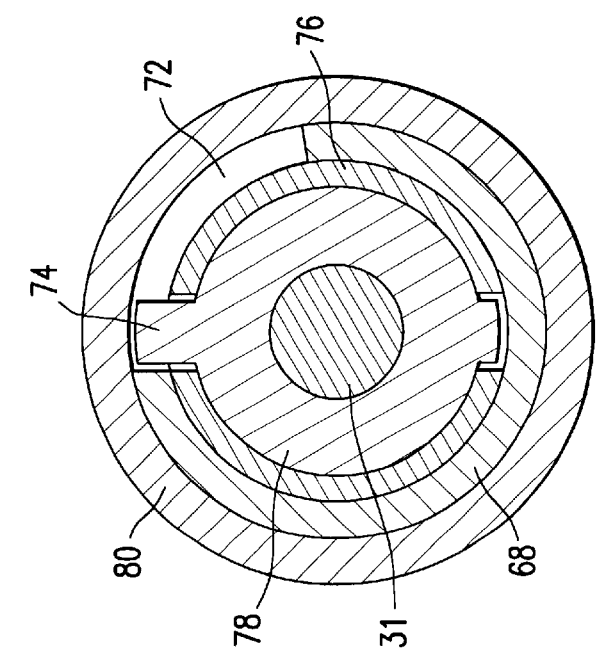
FIG. 15E
FIG. 15F

TISSUE ACCESSING AND ANCHORING DEVICE AND METHOD

RELATED APPLICATIONS

This application is a continuation-in-part of copending application Ser. No. 09/146,185, filed Sep. 1, 1998 now U.S. Pat. No. 6,540,693, application Ser. No. 09/159,467, filed Sep. 23,1998, now U.S. Pat. No. 6,261,241, application Ser. No. 09/356,187, filed Jul. 16, 1999, now U.S. Pat. No. 6,312,429, application Ser. No. 09/477,255, filed Jan. 4, 2000 now U.S. Pat. No. 6,471,700, and application Ser. No. 09/727,112, filed Nov. 29, 2000 now U.S. Pat. No. 6,638,234, all of which are herein incorporated by reference in their entirety.

BACKGROUND OF THE INVENTION

The invention relates to the field of medical devices and methods used in the treatment of diseases such as cancer which have the ability to metastasize within a patient's body. More specifically, the invention is directed to methods and devices for accessing sentinel lymph nodes associated with a lesion site within a patient's body and anchoring devices to these nodes accessed so that they may thereafter be selectively removed and analyzed to determine whether disease has spread from the primary lesion site to the sentinel lymph nodes. In the case of breast cancer patients, such methods and devices may eliminate the need for complete axillary lymph node dissection in patients who do not require such invasive and debilitating procedures.

Metastasis, or migration of cancerous cells, typically occurs through lymph ducts. Sentinel lymph nodes are so-called because, where metastasis occurs, such lymph nodes are often the first locations to harbor metastatic cancer cells. These lymph nodes thus serve as sentinels warning of the spread of the cancerous lesion. A sentinel lymph node may be identified by injection of radioactive material into a primary lesion site such as a cancerous tumor. Detection of radiation at a location other than the injection site indicates that migration of the radioactive material has occurred. The first lymph nodes into which the radioactive material migrates are thus identified as the sentinel lymph nodes.

With regard to breast cancer patients specifically, the determination of the severity of the disease or staging is frequently determined by the level of lymph node involvement in those lymph nodes which correspond to the primary cancer lesion site in the breast. The lymph nodes which correspond to the breast area are typically located in the armpit or axilla of the patient and are connected to the breast tissue of the patient by a series of lymph ducts. Other likely areas for sentinel nodes include inframammary and sub-mammary locations and elsewhere in the patient's chest. The sentinel lymph nodes can be in fluid communication with other surrounding lymph nodes, however, lymph drainage from the lesion site will first flow to the sentinel lymph nodes. Thereafter, lymph fluid drainage may then continue on to lymph nodes surrounding the sentinel nodes.

Studies have shown that by the time a typical breast cancer lesion reaches the size of 1–2 cm, the cancer will have metastasized to at least one of the sentinel lymph nodes in about one third of patients. Malignant cells break off and drain through the lymph fluid ducts to the lymph nodes and will be apparent in excised lymph nodes if the malignant cells embed in the lymph node. In patients with more advanced disease, the likelihood of spread to sentinel nodes is higher as is the likelihood of spread of the disease to the lymph nodes surrounding the sentinel lymph nodes.

As discussed above, when a tumor lesion is under 1–2 cm, only about ⅓ of patients will have cancer cells in the corresponding lymph nodes, and in the patients where the disease has spread to the lymph nodes, it is often confined to the sentinel lymph nodes.

In the past, a breast cancer patient would normally have a complete axillary lymph node dissection as an adjunct to removal of the primary lesion in the breast. Thus, the patient's entire lymph node system in the armpit area is removed and biopsied to determine the stage of the cancer and what further treatment was required. However, as discussed above, when the lesion is under 1–2 cm, two thirds of the patients had no migration of cancer cells to the lymph nodes at all, and in others, cancer had only migrated to the sentinel lymph nodes. Thus, total axillary lymph node dissection in two-thirds of the cases were unnecessary. It should be noted that total axillary lymph node dissection can be an extremely painful and debilitating procedure for patients who often suffer from severe lymph edema as a result of the body's inability to channel the flow of lymph fluid once most or all of the lymph nodes have been excised.

Wires and other devices have been used to anchor devices and to mark suspected cancerous lesion sites within a breast. Such wires may have exposed, sharp ends to cut into tissue, and may expose physicians to accidental injury during excision of tissue. Placement of such marking and anchoring devices is typically performed in the operating room. However, there is a need for methods and devices that can be used to determine the location of sentinel lymph nodes corresponding to a patient's primary lesion site, in addition to the primary lesion site itself, and a reliable means of accessing the sentinel lymph nodes to determine whether they are involved in the disease. If the sentinel lymph nodes are determined not to have cancer cells within them, then a total axillary lymph node dissection may be avoided. Anchoring devices near to such sentinel nodes would be useful if the sentinel lymph nodes are determined to be involved in the disease.

Radioactive materials have been used as localizing agents which can be injected into the area of a primary lesion to monitor the flow of the materials within the patients body using a variety of detectors. A pharmaceutically-acceptable solution containing a radioactive material may be termed a radiopharmaceutical. Suitable radioactive materials include the radioactive elements Technetium 99, Indium 111, Iodine 123 or Iodine 125.

Although techniques exist to locate the sentinel lymph nodes of a patient with such radiopharmaceutical tagging, what has been needed are methods and devices to precisely access the sentinel lymph nodes of the patient and to anchor a device adjacent sentinel lymph nodes should it be determined that axillary node dissection is necessary.

SUMMARY OF THE INVENTION

The invention is directed generally to devices, methods and systems for accessing and anchoring specific target sites within the body of a patient. More specifically, the invention is directed to accessing and anchoring a sentinel lymph node of a patient which corresponds to a lesion site within the patient's body. The accessing and anchoring device may be used to locate a sentinel lymph node during a surgical procedure in which a sentinel lymph node is surgically removed with the anchor device attached.

The accessing and anchoring device having features of the invention has an elongated shaft, with a tissue cutting member, one or more anchoring elements, and may be configured so that at least a portion of a radiation detector may be disposed at or near the distal end of the shaft to aid in radioactive node location. The anchoring element or elements may extend away from the shaft from a position at or near the distal end of the shaft to form a curved or coiled structure or structures which may extend through at least 180°, preferably through at least 360°, and more preferably through at least 540°. In further embodiments of the invention, there are at least two, and more preferably at least three radially extending anchoring elements, which may extend along a substantial length of the shaft. This substantial length of the shaft may further have an oblong transverse cross section.

The tissue cutting member is configured to cut tissue, having a cutting surface which may have a cutting edge. The tissue cutting member may be an electrode, and in particular may be an electrode with an electrosurgical active surface, which may have a sharp edge. This electrode may be configured to be electrically connected to an RF energy source. The cutting surface of the cutting member is preferably spaced from the distal end of the shaft, and may also have an arcuate shape. The elongated shaft of the accessing and anchoring device may have an inner lumen in which an elongated radiation detector may be slidably disposed to an operative location on the distal section of the shaft to facilitate receiving radioactive emissions from a patient's node.

Another embodiment of the tissue accessing and anchoring device has an elongated shaft with a distal portion having an oblong transverse cross section. A plurality of anchoring elements extending along the oblong transverse cross-sectional portion of the shaft, preferably in a parallel relationship, and may extend along the long dimension of the oblong transverse cross sectional portion of the shaft.

Detection of radiation in order to identify sentinel lymph nodes may be accomplished by manipulating the shaft and/or the radiation energy detector to detect the amount of radiation energy emanating from the tissue along the longitudinal axis of the shaft, and comparing the amounts of radiation detected from various portions of tissue. Confirmation that the distal end of the shaft is within or adjacent to a sentinel lymph node is indicated by detecting an above-normal amount of radiation energy emanating from the tissue. Such radiation detection is preferably effected with an elongate radiation detector disposed within the inner lumen of the elongated shaft; most preferably, the elongated radiation detector is slidably disposed within the inner lumen of the elongated shaft. A gamma camera, ultrasound imaging, stains, dyes, or skin markings may be used to determine the approximate position of the at least one sentinel lymph node within the patient's body.

The method of accessing and anchoring a sentinel lymph node of a patient which corresponds to a lesion site within the patient's body generally includes, first locating the approximate position of a sentinel lymph node that has accumulated radioactive material using a radiation detector; accessing the sentinel lymph node; and then anchoring the node. The node may be accessed by activating the tissue cutting member on the distal end of the device to ablate tissue while passing the shaft into the patient's body until the distal end of the shaft is disposed within or adjacent to the sentinel lymph node. One or more anchoring elements are extended from the shaft into the sentinel lymph node to secure the distal end of the device to the sentinel lymph node. The step of extending an anchoring element may include a radially extending step, and may further include the step of activating an outer extremity of an anchoring element to emit radiofrequency (RF) energy as it extends. The methods may also include locating a sentinel lymph node using the accessing and anchoring device during a surgical procedure in which a sentinel lymph node is surgically removed with the accessing and anchoring device attached.

The system for accessing and anchoring a sentinel node within a patient includes the previously described accessing and anchoring device with an elongated radiation detecting member slidably disposed within the lumen of the shaft so that radiation detecting elements are located near enough to the distal end of the device to detect radiation emitted from a radioactive sentinel lymph node. The system may further include an electrical lead electrically coupled to a radially extending anchoring member, and another electrical lead electrically coupled to the patient. In this way, RF energy from a RF source can be applied to an anchoring element during its deployment and extension.

The devices, methods and systems of the invention provide the advantages of locating and accessing a desired location within a patient's body with a single device which may be directly anchored at the location. Including these capabilities in a single device avoids the delay and imprecision in anchoring a device at a proper location that results from the use of multiple devices for these functions. Moreover, the methods and devices of the present invention are suitable for use outside of an operating room, simplifying and reducing the cost of such procedures. In addition, the coiling of the anchoring elements serves to shield the sharp tips, protecting physicians from possible injury during excision of a patient's tissue. The present invention thus provides improved devices for marking and excising a sentinel lymph node that has accumulated radiation and is suspected of harboring cancerous tissue. In addition, the devices provide anchoring elements that radially extend through a substantial angular extent to provide improved anchoring and demarcation of a location within a patient's body.

These and other advantages of the invention will become more apparent from the following detailed description when taken in conjunction with the accompanying exemplary drawings.

BRIEF DESCRIPTION OF THE DRAWINGS

FIG. 1B is a perspective view of a system embodying features of the invention with anchoring elements deployed.

FIG. 13A illustrates an anchoring element and anchoring element sheath embodying features of the invention following deployment of the anchoring element from a stationary sheath.

FIG. 13B illustrates an anchoring element and anchoring element sheath embodying features of the invention following deployment of the anchoring element from a retracting sheath.

FIG. 13C illustrates an anchoring element and anchoring element sheath embodying features of the invention following deployment of the anchoring element from a sheath that was first held stationary and then retracted.

FIG. 14A illustrates an anchoring element embodying features of the invention having a blunt tip.

FIG. 14B illustrates an anchoring element embodying features of the invention having a barbed tip.

FIG. 15D is a transverse cross-sectional view taken along line 15D—15D of the tip portion of the device of FIG. 15A.

FIG. 15E is a transverse cross-sectional view taken along line 15—15E of the device of FIG. 15A.

FIG. 15F is a transverse cross-sectional view taken along line 15F—15F of the device of FIG. 15A.

FIG. 16G is a transverse cross-sectional view taken along line 16G—16G shown in FIG. 16C.

DETAILED DESCRIPTION OF THE INVENTION

Figure 1A:
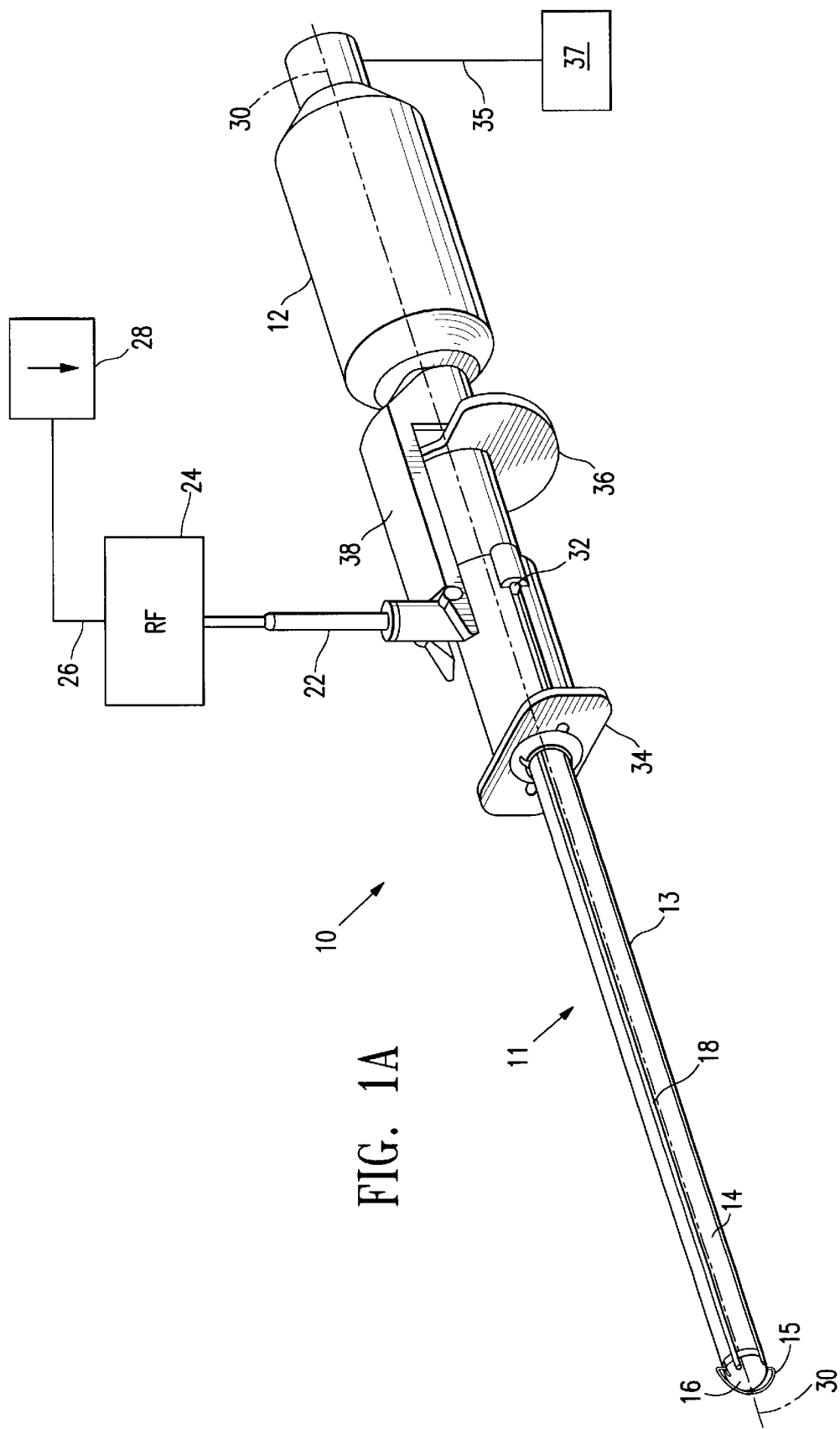
FIG. 1A is a perspective view of a system embodying features of the invention, with anchoring elements retracted.

FIGS. 1A and 1B show a system 10 embodying features of the invention, which includes a sentinel node accessing and anchoring device 11, and an elongated radiation detector 12. The accessing and anchoring device has a shaft 13 with a proximal portion and a distal portion 14 with a cutting wire 15 at its tip 16; and a source of radio frequency (RF) power 24 connected to the cutting wire 15 via RF connector 22. The shaft 13 and radiation detector 12 lie generally along longitudinal axis 30. As shown in FIGS. 1A and 1B, cutting wire 15 is a tissue cutting member that may be activated by RF energy and is configured to ablate and penetrate tissue. It is shown as an arcuate wire spaced distally from the tip 16 of shaft 13. In alternative embodiments, cutting wire 15 may take other shapes and may be in contact with or form part of tip 16.

Figure 4:
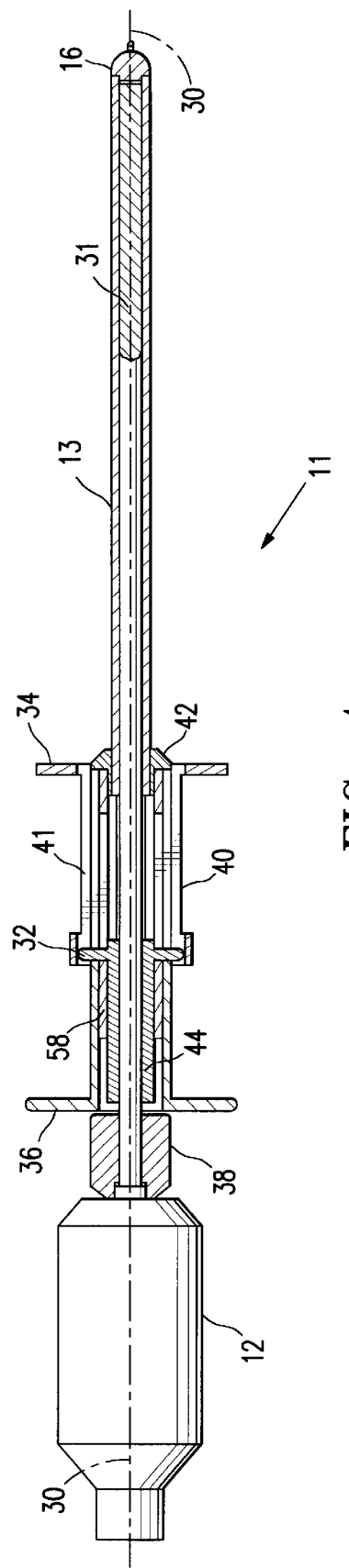
FIG. 4 is a top cross-sectional longitudinal view of the device shown in FIG. 2.
Figure 5B:
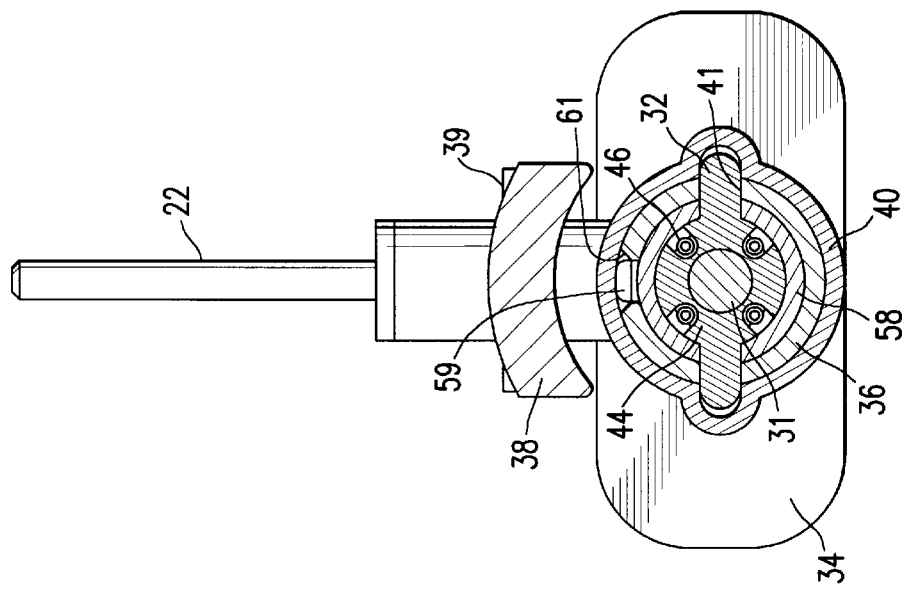
FIG. 5B is a rear elevation view of the device of FIG. 2 including a transverse cross-sectional view of the shaft of the device taken along line 5B—5B of FIG. 2.
Figure 5A:
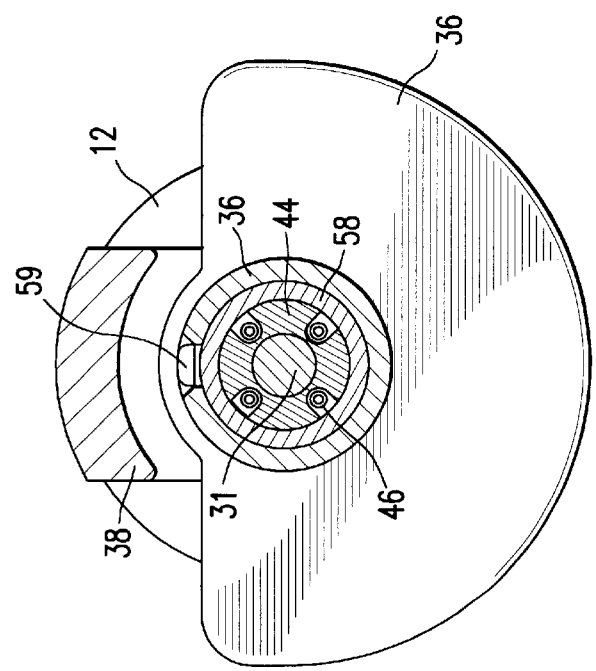
FIG. 5A is a front elevation view of the device of FIG. 2 including a transverse cross-sectional view of the shaft of the device taken along line 5A—5A of FIG. 2.
Figure 5D:
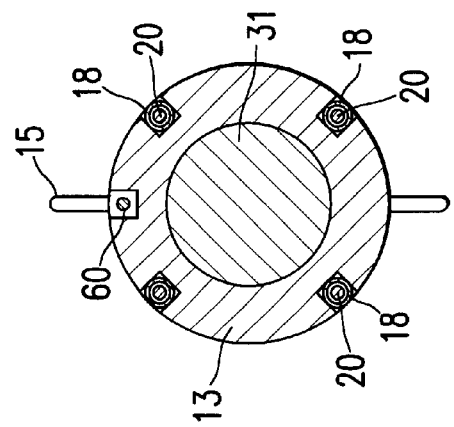
FIG. 5D is a transverse cross-sectional view of the shaft of the device of FIG. 2 taken along line 5D—5D of FIG. 2.
Figure 5C:
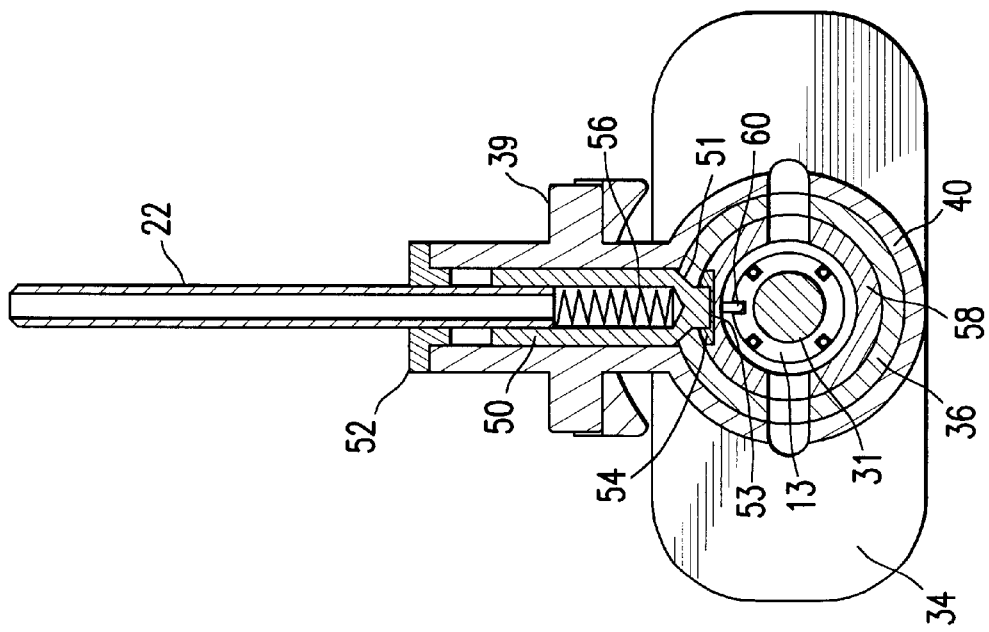
FIG. 5C is a rear elevation view of the device of FIG. 2 including a transverse cross-sectional view of the shaft and RF-power connector taken along line 5C—5C of FIG. 2.
Figure 6:
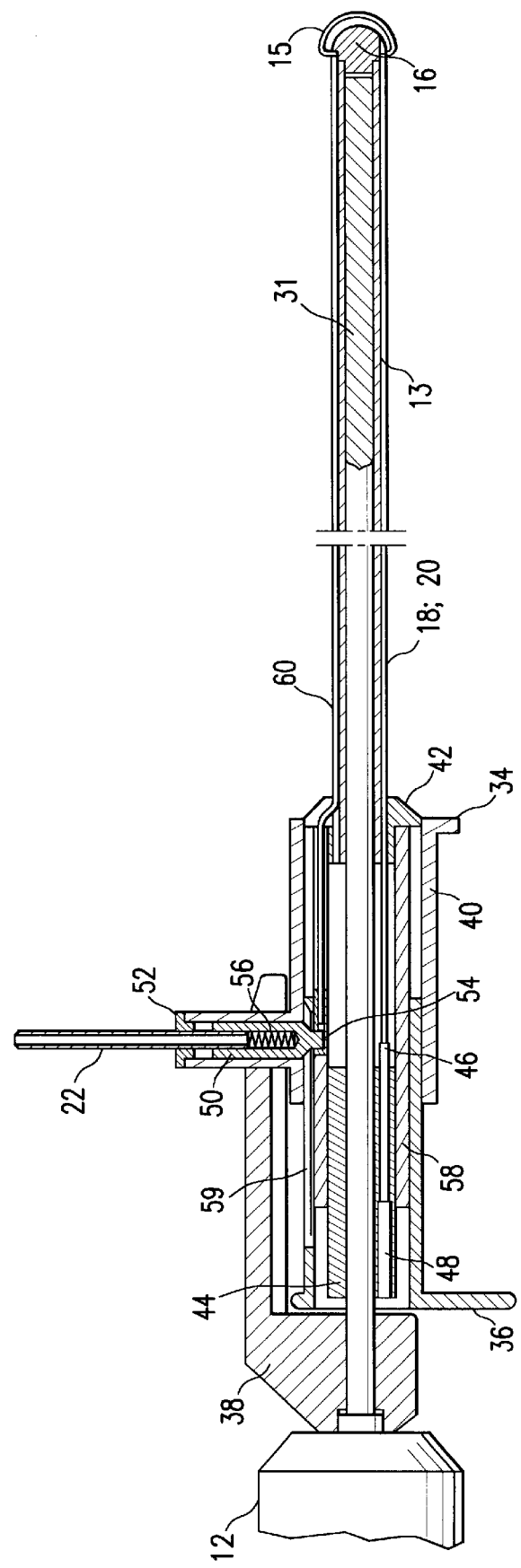
FIG. 6 is a side elevation view in partial longitudinal section taken along line 6—6 of FIG. 3.

Radiation energy detector 12 includes an elongated probe 31, shown in FIGS. 4 and 6, and may be, e.g., a gamma probe. Radiation energy detector probe 31 is effective to detect, locate and identify a lymph node within a patient's body that has accumulated radioactive material and is emitting radiation. Detection of radiation by detector 12 is communicated via cable 35 to signal processor 37 and thereby to an operator. The electrical circuit pathway from RF power source 24 to cutting wire 15 is completed by ground connector 26 and ground pad 28, which may be placed in contact with a patient. As shown in FIGS. 1A and 1B, the RF electrode (cutting wire 15) may lie in substantially the same plane as the longitudinal axis 30 of the elongate shaft of the node accessing and anchoring device 11, although it need not do so in every embodiment.

As shown more clearly in FIG. 1B, anchoring elements 20 may be deployed from anchor sheaths 18 at tip 16 to anchor the device 11 in position within a patient's body. In the embodiment shown in FIG. 1B, anchoring elements 20 extend in a radial direction from the tip 16 of shaft 13. By "radial" is meant a direction that is angled, and may be generally orthogonal, to a longitudinal axis 30 of the shaft 13 or an axis of an anchoring sheath 18, so that a line passing within the coils is angled with respect to such a longitudinal axis. Anchoring elements 20 are deployed by movement of the thumb rest 36 towards finger rest 34 (note changed positions of tab 32 and thumb rest 36 between FIGS. 1A and 1B). Anchoring elements 20, when deployed, are effective to secure device 11 in a desired location within a patient's body, as, e.g., when a sentinel lymph node has been located using the radiation energy detector 12.

Figure 2:
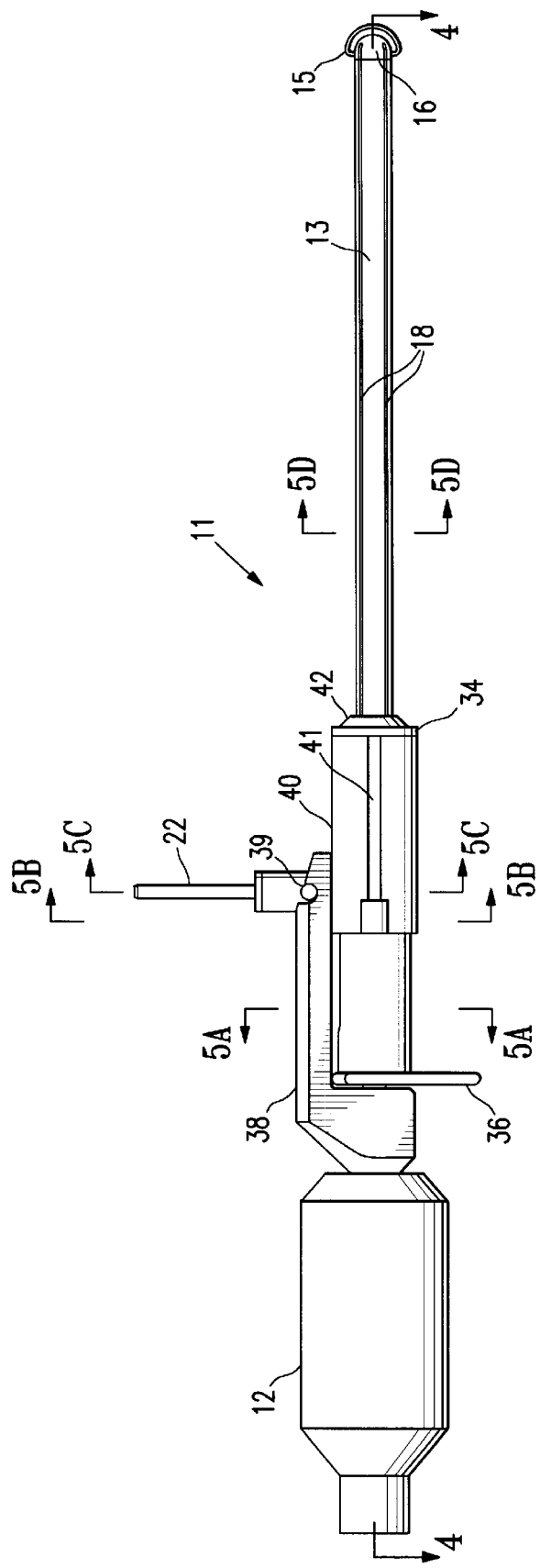
FIG. 2 is a side elevation view showing a device embodying features of the invention with anchoring elements retracted.

FIG. 2 shows a sentinel node accessing and anchoring device 11, with anchoring elements 20 retracted within anchor sheaths 18. Radiation energy detector 12 is attached by latch 38 to shell 40. Latch 38 fits snugly under shell tabs 39 which hold latch 38 and so hold radiation energy detector 12 to the rest of the device. Transition bushing 42 aligns shaft 13 with shell 40.

Figure 3:
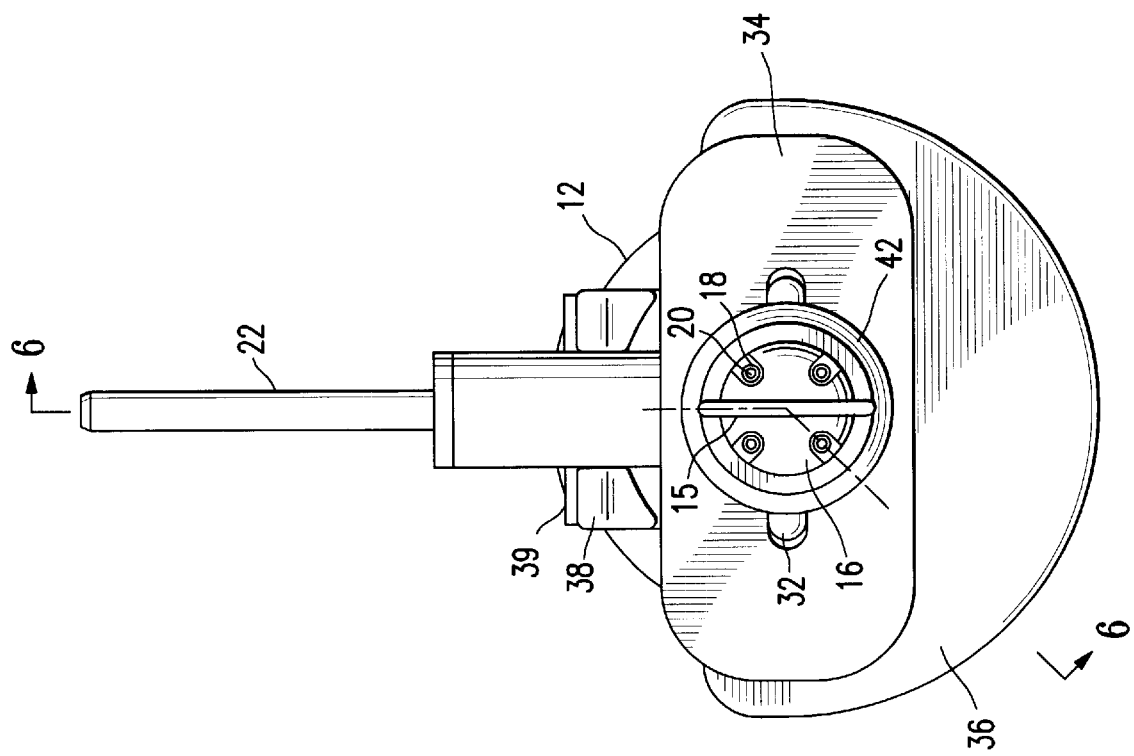
FIG. 3 is a front elevation view of the device of FIG. 2.

FIG. 3 shows the device 11 from the front, showing cutting wire 15 lying in a plane aligned with RF connector 22 and in substantially the same plane as the longitudinal axis 30 of the shaft 13.

The positioning of radiation energy detector 12 and its elongated probe portion 31, which is slidably disposed within shaft 13 and extends within shaft 13 to the distal portion 14 and may extend up to tip 16, adjacent a patient's lymph nodes allows the detection of radiation (such as gamma radiation), if any, emitted from material collected within a sentinel lymph node of a patient, and so allows the identification of sentinel lymph nodes in a patient at risk of cancer metastasis. Radiation energy detector 12 detects radiation energy emanating from the tissue along longitudinal axis 30 in a proximal direction relative to radiation energy detector probe 31. The hollow shaft 13 or the radiation energy detector probe 31 within the shaft 13 can be manipulated while within a patient to detect the amount of radiation energy emanating from various portions of the tissue as they pass in front of the tip 16 and into the radiation energy detector 12 during the manipulation.

The amount of radiation detected from the various portions of tissue adjacent the longitudinal axis 30 of the device 11 and shaft 13 can be used to determine the position of the radiation energy detector 12 that produces the maximum radiation signal strength. The output of a radiation energy detector such as a detector 12 is carried by cable 35 to provide, e.g., a visual or audio signal or the like generated by a signal processor 37. Such an output may be observed and used by an operator of the system to determine the relative or the absolute amounts of radiation detected at a particular position within a patient's body. The input of the radiation energy detector probe 31 within the tip 16 of the shaft 13 can be configured so as to maximize output signal strength when a sentinel lymph node that emits a relatively large amount of radiation ("hot" sentinel lymph node) is disposed directly distal of the tip 16 of the shaft 13 and radiation energy detector probe 31. Thus, by maximizing the output signal from the detector 12, the operator can determine the precise location of a hot sentinel lymph node and effectively discriminate surrounding non-radioactive tissue and non-radioactive nodes.

As illustrated in FIGS. 4 and 5, at least a portion of the radiation energy detector 12 fits inside shaft 13. The device 11, shaft 13, and elongate portion 31 of radiation energy detector 12 may all share a common longitudinal axis 30. In embodiments or the invention, elongate portion 31 fits slidably within shaft 13. The diameter of an elongate portion 31 of the radiation energy detector 12 configured to fit within shaft 13 can be about 1 to about 6 mm, specifically about 3 to about 5 mm, and more specifically about 4.0 to about 4.4 mm. A detector body is disposed within the elongate portion 31 of radiation energy detector probe 12 which is configured to receive radiation energy at an angle of up to about 30°, preferably about 10° to about 20°, from a longitudinal axis 30 of the elongate portion 31 of the radiation energy detector probe 12. The detector body can be designed to encompass the radiation emitted from a 1 cm node at a distance of 1 cm. The detector body can be configured to have enhanced reception of radiation energy from the distal end 14 of the device 11 as opposed to side impingement of radiation energy. The detector body is coupled by the cable 35 to the signal processor unit 37. The detector body can be configured to specifically detect gamma radiation or any other suitable form of radiation energy including alpha or beta radiation. Radiation energy detector 12 may have a preamplifier within it to increase the signal from the detector body to the signal processor unit 37. The length of the radiation energy detector probe 31 is typically configured to access radiation emitted from a patient's tissue through a hollow shaft that can be, e.g., about 5 to about 15 cm long.

The signal processor unit 37 connected to the radiation energy detector 12 can be configured to emit an audible signal to be detected by a user of the detector which has a volume and/or frequency which increases in relation to an increase in the amount of radiation energy being detected. Alternatively, the signal processor unit 37 can produce a visual signal to be detected by a user of the detector which is proportional in amplitude to the amount of radiation energy being detected. For example, a signal processor 37 may provide a digital readout of counts per second and total counts for given time period. It will be understood that other methods for communicating a signal from signal processing unit 37 to an operator may also be used. The radiation energy detector 12 can typically detect radiation at useable levels from a hot lymph node from a distance of up to about 10 to about 12 cm or more, but is more accurate at shorter distances, such as distances less than about 8 cm to about 10 cm, and is most accurate at distances of about 2 to about 3 cm.

Preferably, the location of a sentinel lymph node identified by radiation detector 12 must be marked so that it may be excised. As shown in FIG. 1B, anchoring elements 20 may be deployed from anchor sheaths 18 at tip 16 to anchor the device in position, thereby marking the proper location. In the embodiment shown in FIG. 1B, anchoring elements 20 extend in a radial direction from the tip 16 of shaft 13. In embodiments of the invention, anchoring elements 20 deploy from positions at or very near to tip 16; in further embodiments, anchoring elements may deploy from positions proximal of tip 16.

Anchoring elements 20 are deployed by movement of the thumb rest 36 towards finger rest 34 (note changed positions of tab 32 and thumb rest 36 between FIGS. 1A and 1B). As illustrated in the figures, in preferred embodiments, a sentinel node accessing and anchoring device 11 is configured to be easily held in one hand by an operator. The anchoring elements may be deployed by squeezing and moving the thumb (on the thumb rest 36) towards the fingers (on the finger rest 34). The fingers remain stationary as the thumb and thumb rest 36 approach the fingers and finger rest 34, insuring that the tip 16 remains stationary as the anchoring elements are deployed.

Thus, the node accessing and anchoring device 11 may be used to access a lymph node with anchoring elements 20 retracted within anchoring element sheaths 18, the presence or absence of radiation detected with radiation energy detector 12 which extends within shaft 13 to tip 16, and, when a sentinel node containing radiation emitting material is detected, the position may be marked by deployment of anchoring elements 20 to fix the device in place for excision of the sentinel node lymph.

Anchoring elements 20 may be formed at least in part from a metal, alloy or compound having shape memory, including a nickel-titanium shape-memory alloy such as nitinol. In preferred embodiments, anchoring elements 20 are formed at least in part from super-elastic nitinol. Alternatively, or additionally, anchoring elements 20 may also include stainless steel or other bio-compatible materials with suitable spring-like properties. Anchoring element sheaths 18 may be made with, among other materials, stainless steel or polymer tubes, such as hypodermic tubes or other sheath material suitable for enclosing and guiding an anchoring element 20 which may assume a fairly linear configuration within the sheath but which, upon deployment from the sheath, assumes a coiled configuration. Anchoring element sheaths 18 may have ends that are flat, rounded, beveled, sharpened, flared, tapered, or that have other configurations. Anchoring elements 20 may extend from the tip 16 by about 1 to about 35 mm, specifically by about 5 to about 30 mm, and more specifically by about 15 to about 25 mm when deployed fully.

The anchoring elements curve and coil as they are deployed, to assume a configuration having a curved structure. In embodiments of the invention, the curved structure of the anchoring elements 20 extends through at least 180° of curvature; in further embodiments, the curved structure extends through at least 360°; and in yet further embodiments, it extends through at least 540°; and in still further embodiments, the curved structure of the anchoring elements 20 extends through more than 540°.

FIGS. 4 and 6 show the cylindrical portion of thumb rest 36 in contact with push sleeve 44. Connected to push sleeve 44 is push sleeve tab 32 which slides within slot 41 in shell 40 and shows the location of push sleeve 44. Housing 58 is located between and separates thumb rest 36 and push sleeve 44 providing support and guidance as push sleeve 44 advances to push anchoring element bushing 48 and so to deploy anchoring elements 20 by causing them to move within anchoring element sheaths 18 located in anchoring element support sleeves 46.

FIGS. 5A–D provide illustrations of cross-sections of the device 11 at the locations indicated by lines 5A—5A (for 5A), 5B—5B (for 5B), 5C—5C (for 5C) and 5D—5D (for 5D) of FIG. 2. Shown in these figures are support sleeves 46 in which anchoring element sheaths 18 slide. Support sleeves 46 and anchoring element sheaths 18 together enclose anchoring elements 20 in a variable-length enclosure. Sleeves 46 and sheaths 18 fit together with part of one inside part of the other so that they may slide and telescope to maintain an enclosure around anchoring elements 20 regardless of the total length of the enclosure. Support sleeves 46 and anchoring element sheaths 18 are configured to support and encase anchor wire 20 along its length, and to prevent buckling of anchor wire 20.

In further embodiments of the invention, the shaft 13 has an oblong transverse cross-section. The anchoring elements 20 may further include or contact conductors connected to a source of RF power 24, and an actuator coupled to the conductors or directly to the anchoring elements 20 for extending the anchoring elements 20. Conductors for connecting anchoring elements 20 and/or cutting wire 15 with a source of RF power 24 are termed "inner conductors" since they may extend along an inner portion of the shaft 13 or within anchoring element sheaths 18, or within other elements of devices embodying features of the invention. For example, cutting wire connector 60 is an inner conductor. An inner conductor may contain an inner lumen, which may contain a shaft. Anchoring elements may be deployed by an actuator that is coupled to the inner conductor.

In embodiments where anchoring elements 20 are operably connected to an RF power source 24, anchoring elements may be insulated, by being coated with an insulating coat or being sheathed with an insulating sheath so as to cover most but not all of the surface of the anchoring element that may come into contact with body tissue. Application of RF power to an anchoring element 20 having an uninsulated tip and insulation along most of its length is effective to ease the entry of the anchoring element into body tissue as the anchoring element 20 is deployed. Any biocompatible insulating material, such as a polymer (e.g., polyimide) is suitable for insulating an anchoring element 20.

In embodiments of the invention, the source of RF power 24 is switchable, and the connection may be a switchable connection. Thus, in embodiments of the invention, RF power source 24 may be capable of providing different levels of RF power, and may be switched between the different levels by the operator. A switchable power source 24 and switchable connections to RF power source 24 thus provide the ability, for example, to provide one amount of power to the cutting wire 15 and another amount of power to anchoring elements 20 as desired. For example, an RF power source 24 may be switchably connected to an inner conductor. In addition, a switchable RF power source 24 provides the capability to deliver different amounts of power to cutting wire 15 at different times. For example, it may be desirable to provide cutting wire 15 with different amounts of power depending upon different types of tissue encountered within the body of a patient.

FIG. 6 illustrates the linkage between RF connector 22 and cutting wire contact 54. This linkage is also illustrated in FIGS. 11 and 12. RF connector 22 is held in contact with compression spring 56 within sliding pin 50. This assembly is retained within shell 40 by retainer 52. Sliding pin 50 is pressed against cutting wire contact 54 by the action of compression spring 56 to make an effective electrical connection between RF power source 24 and cutting wire 15 via RF connector 22, compression spring 56, sliding pin 50, cutting wire contact 54 and cutting wire connector 60. Cutting wire connector 60 bends within transition bushing 42 as shown in FIG. 12B to extend along the length of shaft 13 to contact cutting wire 15 at tip 16.

In addition to providing electrical contact between RF cable 22 and cutting wire contact 54, sliding pin 50 also provides a mechanical connection between shell 40 and the probe assembly that includes shaft 13 and housing 58. Depression of latch 38 to release tabs 39 allows the removal of the radiation energy detector 12.

As shown in FIG. 5, thumb ring 36 has a slot 59 having a chamfer 61 along a portion of the wall of slot 59. Sliding pin 50 has a bevel 51 near its contact tip 53 that mates with slot wall 61 (in slot 59) that has a chamfer, or an angle with respect to the surface of thumb ring 36. Sliding pin 50 is held in secure electrical contact with cutting wire contact 54 by compression spring 56 when inserted into those portions of slot 59 with a slot wall 61 having a chamfer. The most proximal portion of slot 59 has a slot wall 61 with no chamfer, instead having a slot wall 61 that joins the surface of thumb ring 36 in a configuration that is substantially perpendicular to that surface, as shown in FIG. 11A. Sliding thumb ring 36 forward towards finger rest 34 moves the position of contact tip 53 of sliding pin 50 towards more proximal portions of slot 59. Contact between contact tip 53 and cutting wire connector 60 is maintained as long as sliding pin 50 is within a portion of slot 59 that has a chamfer 61. However, electrical contact between sliding pin 50 and cutting wire connector 60 is lost as thumb ring 36 nears its most forward position, causing sliding pin 50 to move to a position where bevel 51 contacts a slot wall 61 that has no chamfer. There, contact between bevel 51 and the outer surface of thumb ring 36 lifts sliding pin 50 as slot 59 is moved distally with respect to sliding pin 50. Raising or removal of sliding pin 50 allows the removal of shell 40, thumb ring 36, finger rest 34, and other associated elements from housing 58 (including radiation energy detector probe 12 if still attached to shell 40 with latch 38 connecting to tabs 39). Removal of these elements may be desirable, for example, after the deployment of the anchoring elements to allow marking of the sentinel lymph node for an extended period of time without the weight, bulk and possible discomfort to the patient of the radiation energy detector probe 12, shell 40, and other elements. Such an extended period of time may be up to a few minutes, a few hours, or several hours, depending upon the length of time necessary to effect a full diagnosis of the patient's condition and, where desirable, to effect the removal of the sentinel lymph node and optionally any surrounding structures.

Figure 7:
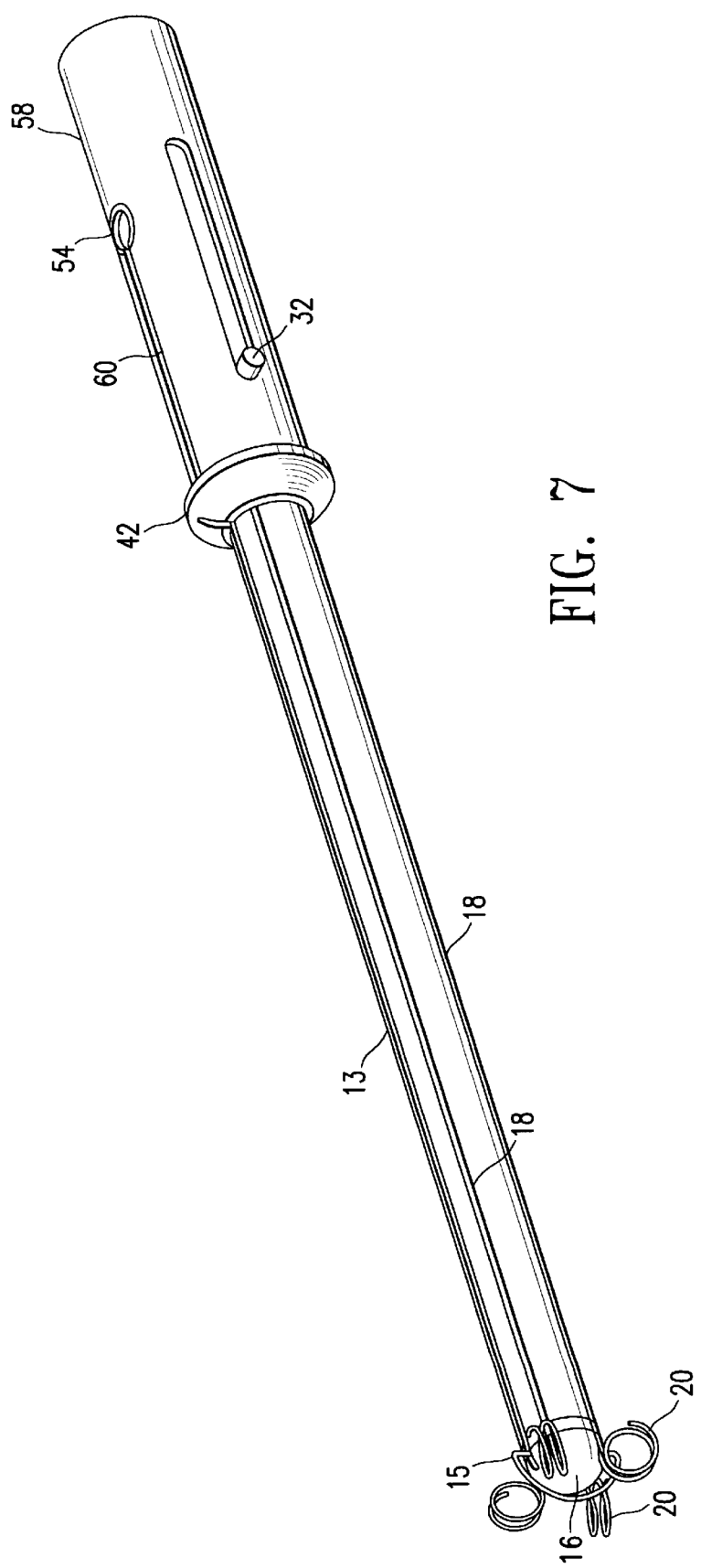
FIG. 7 is a perspective view of a portion of a device embodying features of the invention with anchoring elements deployed.

FIG. 7 illustrates the shaft 13 and housing 58 of a sentinel node accessing and anchoring device embodying features of the invention after detachment of shell 40 and other elements from the shaft 13 and housing 38. The anchoring elements 20 are shown deployed; accordingly, push tab 32 within slot 59 is shown in a forward position. Cutting wire contact 54 is shown in connected with cutting wire connector 60 which runs along shaft 13 to connect with cutting wire 15.

Figure 8:
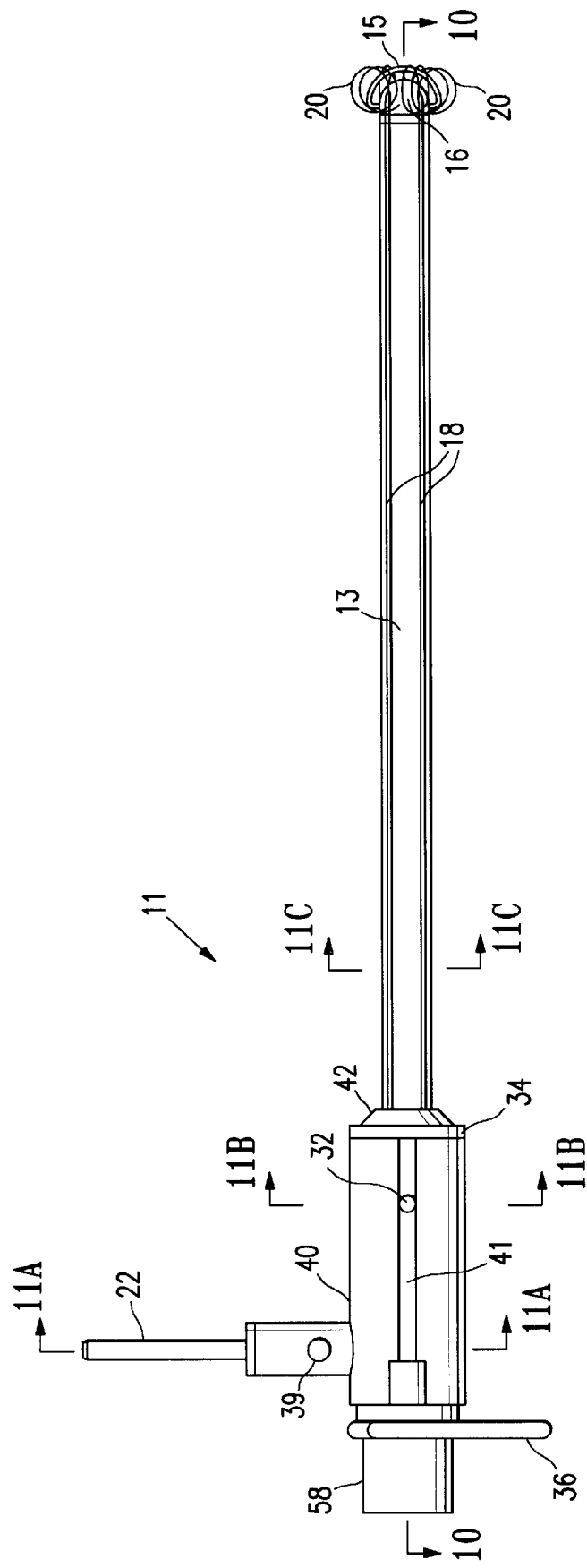
FIG. 8 is a side elevation view of a device embodying features of the invention with anchoring elements deployed.

FIG. 8 shows a sentinel node accessing and anchoring device with anchoring elements 20 deployed. Thumb rest 36 is positioned adjacent shell 40 and push sleeve tab 32 is in a forward position in slot 41 when anchoring elements 20 are deployed. This is in contrast to the configurations of thumb rest 36 and push sleeve tab 32 shown in FIG. 1A and in FIGS. 2–5 with anchoring elements retracted. During use, after location and identification of a sentinel lymph node, and positioning of the tip 16 of the shaft 13 adjacent to the sentinel lymph node, anchoring elements 20 are deployed to fix the device in position. When the device has been fixed in a proper location within a patient's body, there is no longer need for radiation energy detector 12, and it may be removed. For example, latch 38 may be depressed at its distal end to disengage the radiation energy detector 12 from shell tabs 39 and elongated portion 31 of radiation energy detector 12 withdrawn from within shaft 13. Accordingly, no radiation energy detector 12 is shown in FIGS. 8–12, which depict a device embodying features of the invention as it may be used after anchoring elements 20 have been deployed.

Figure 9:
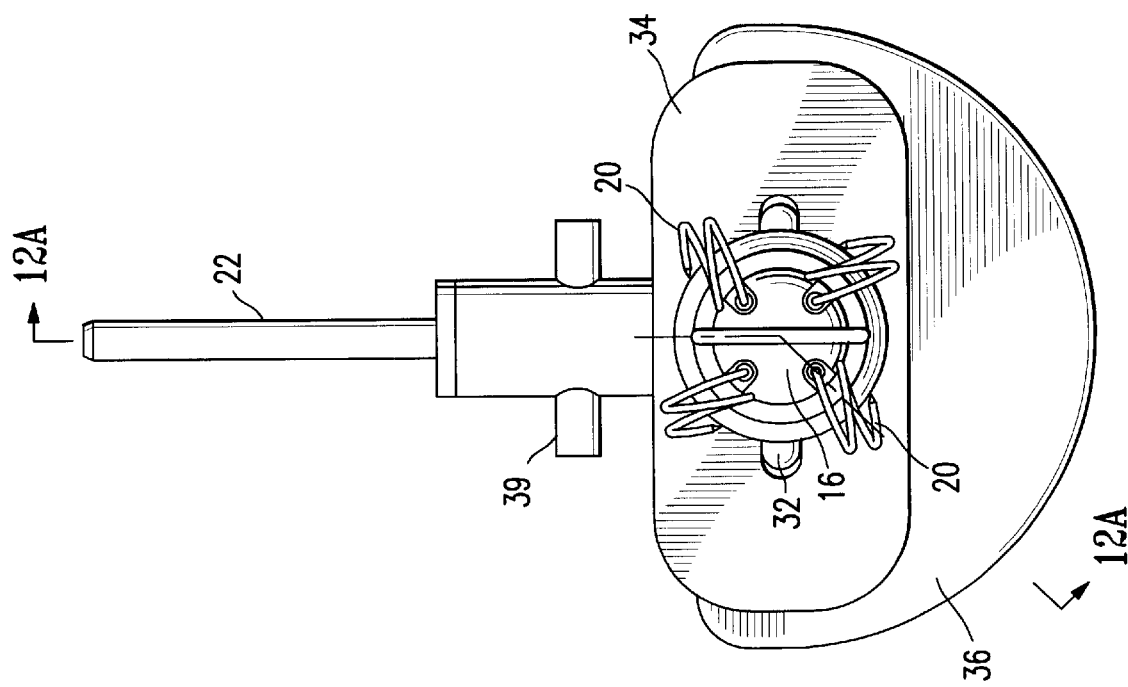
FIG. 9 is a front elevation view of the device of FIG. 8 with anchoring elements deployed.

FIG. 9 shows the device illustrated in FIG. 8 viewing along a longitudinal axis towards cutting wire 15. The anchoring elements 20 are shown in their deployed configuration.

Figure 10:
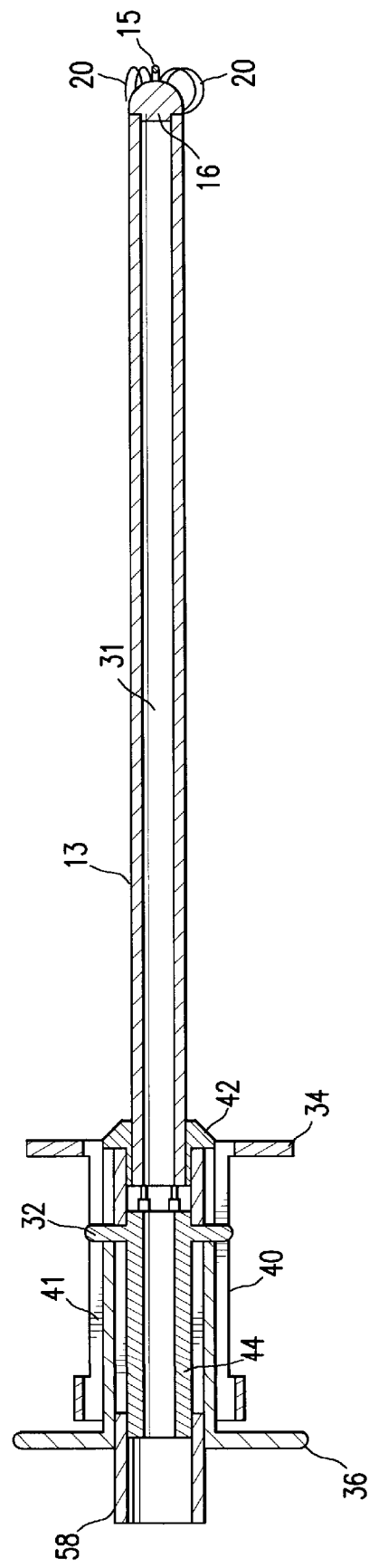
FIG. 10 is a top cross-sectional longitudinal view of the device shown in FIG. 8.

FIG. 10 is a cross-sectional longitudinal view of the device shown in FIG. 8, taken along a plane perpendicular to a line running along RF power connector 22, showing the configuration of the push sleeve 44 within housing 58 and shell 40 when anchoring elements 20 are deployed.

Figure 11B:
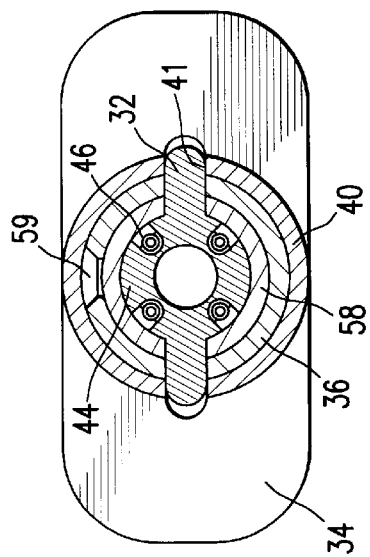
FIG. 11B is a rear elevation view of the device of FIG. 8 including a transverse cross-sectional view of the shaft taken along line 11B—11B.
Figure 11C:
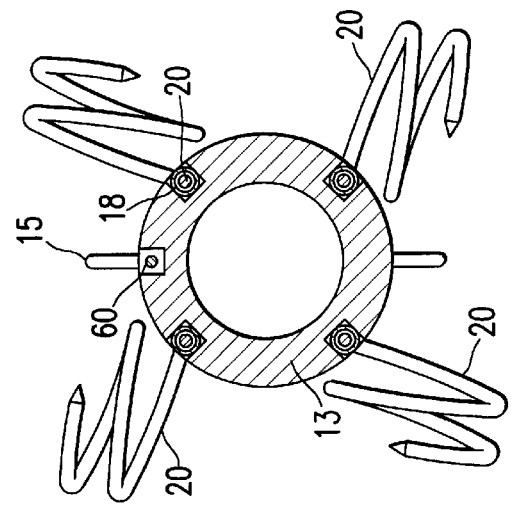
FIG. 11C is a cross-sectional view of the shaft of the device of FIG. 8 taken along line 11C—11C elevation also showing the deployed anchoring elements.
Figure 11A:
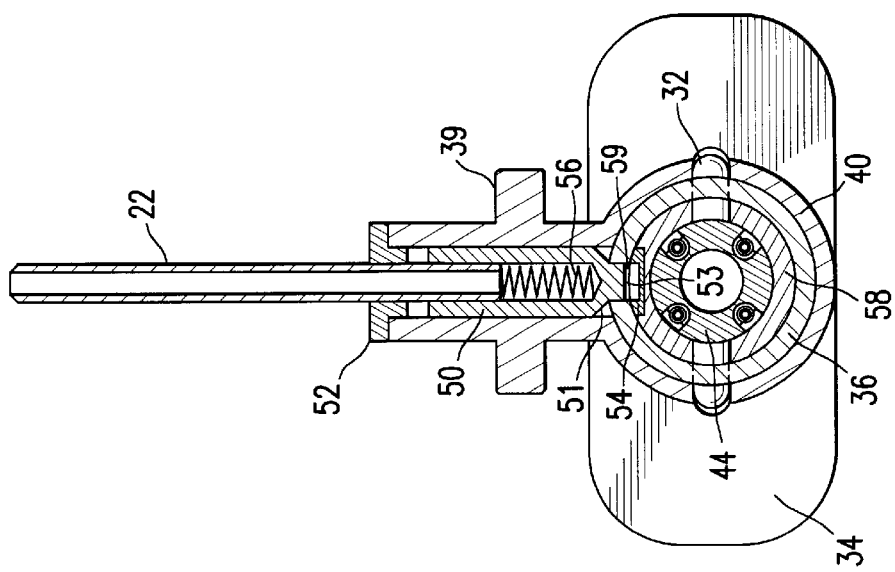
FIG. 11A is a rear elevation view of the device of FIG. 8 including a transverse cross-sectional view of the shaft and RF-power connector taken along line 11A—11A.

FIG. 11 illustrates sectional views of portions of the device shown in FIG. 8. Lines 11A—11A, 11B—11B, and 11C—11C shown in FIG. 8 indicate the lines along which cross-sections are taken and illustrated in FIGS. 11A, 11B and 11C. FIG. 11 illustrates the configuration of elements of a device embodying features of the invention when anchoring elements 20 are deployed. Anchoring elements 20 illustrated in FIG. 11C have sharp tips 64 effective to aid their deployment into tissue of a patient's body. FIGS. 11A and 11B show cross-sections of the shaft 13 and, in FIG. 11A, show the RF power connections and some of its constituent elements in greater detail.

Figure 12A:
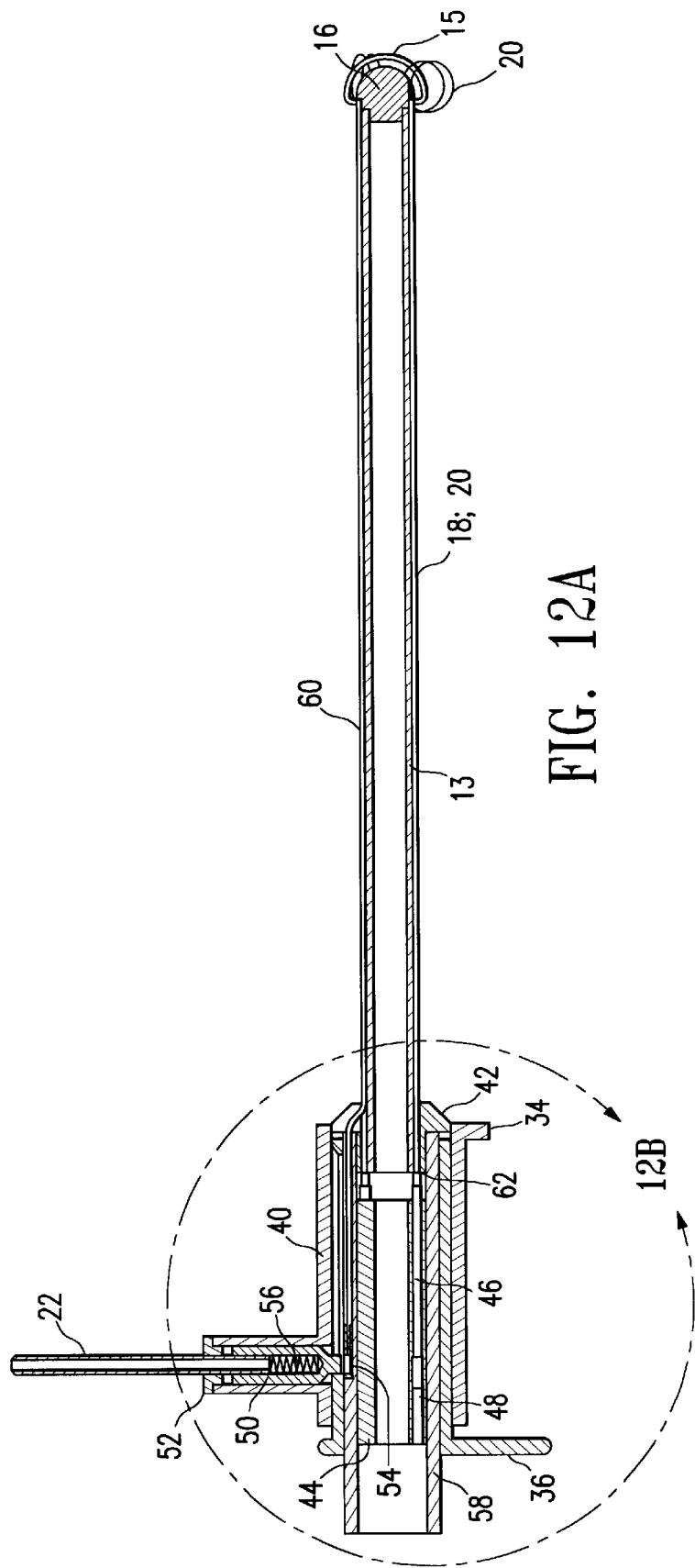
FIG. 12A is a side elevation view in partial longitudinal section taken along line 12A—12A of FIG. 9.
Figure 12B:
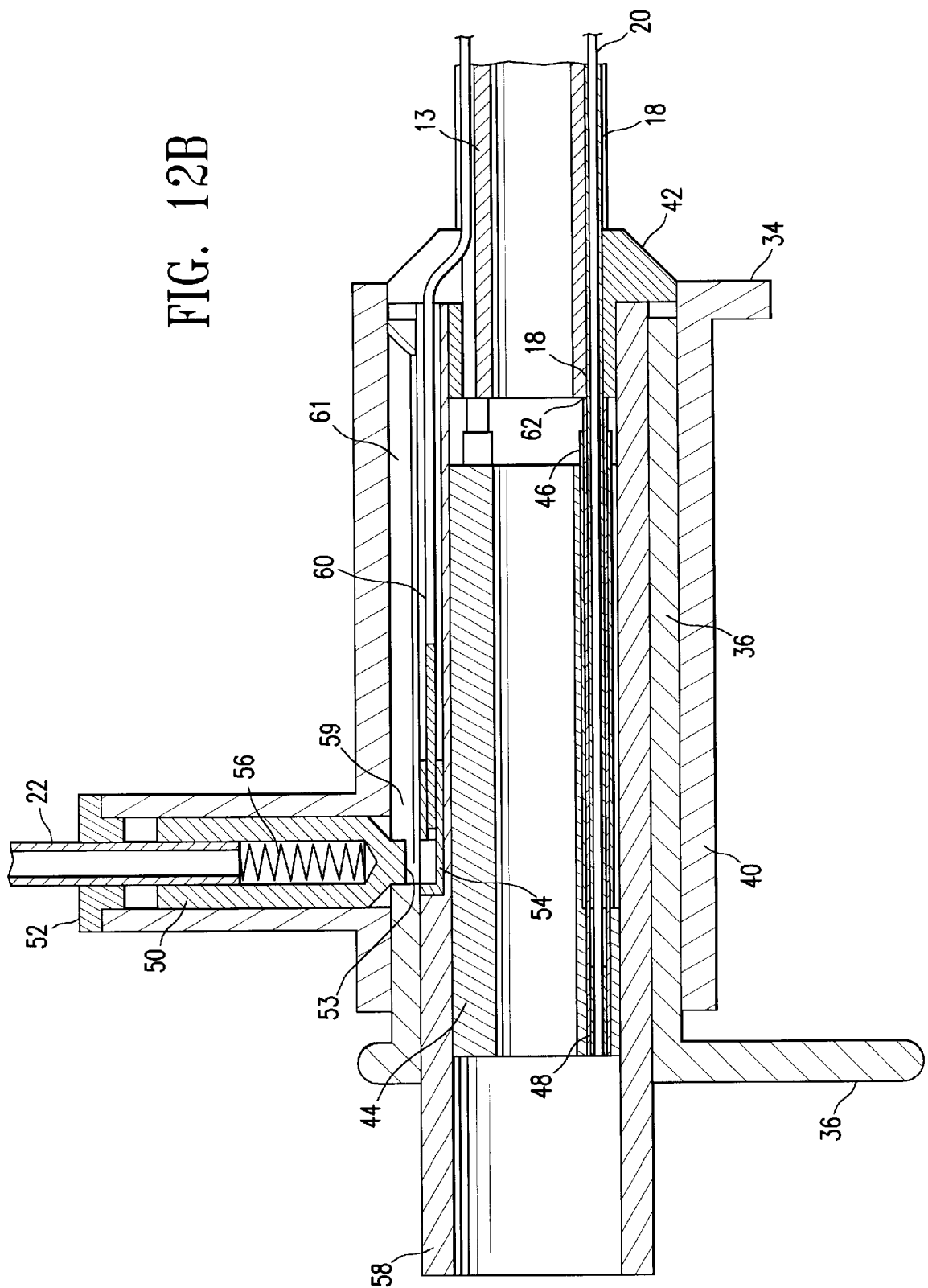
FIG. 12B is a side cross-sectional view of the portion of the device of FIG. 12A within circle 12B.

The broken line 12A—12A in FIG. 9 indicates the section illustrated in FIG. 12A. FIG. 12A is a view of the device of FIG. 8 showing RF connections between RF connector 22, and elements 50, 52, 54, 56 and 60 with cutting wire 15. Circle 12B in FIG. 12A indicates the portion of the figure that is shown in greater detail in FIG. 12B. The RF power connections, as well as the anchoring element bushings 48, are shown in greater detail in FIG. 12B. Also shown in FIG. 12 is a telescoping junction 62 between an anchor element sheath 18 and a support sleeve 46.

Figure 12C:
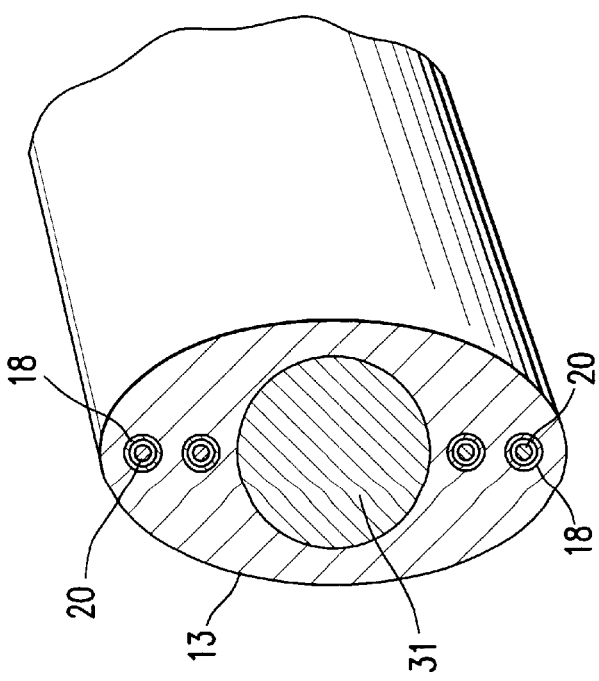
FIG. 12C is a cross-sectional view of a portion of an elongated shaft of a device having an oblong cross-section embodying features of the invention.

The elongated shaft 13 of a device embodying features of the invention may have other than a circular cross-section. For example, as illustrated in FIG. 12C, the elongated shaft 13 of a device 11 embodying features of the invention may have having an oblong cross-section. In the portion of the device 11 illustrated in this figure, multiple anchoring elements 20 are housed within anchoring element sheaths 18 extending along the oblong transverse cross-sectional portion of the shaft 13. Anchoring elements 20 and sheaths 18 are preferably situated in a parallel relationship as shown in FIG. 12C. Elongated portion 31 of radiation energy detector 12 also extends along the long dimension of the oblong transverse cross-sectional portion of the shaft 13 in the embodiment shown.

Figure 12D:
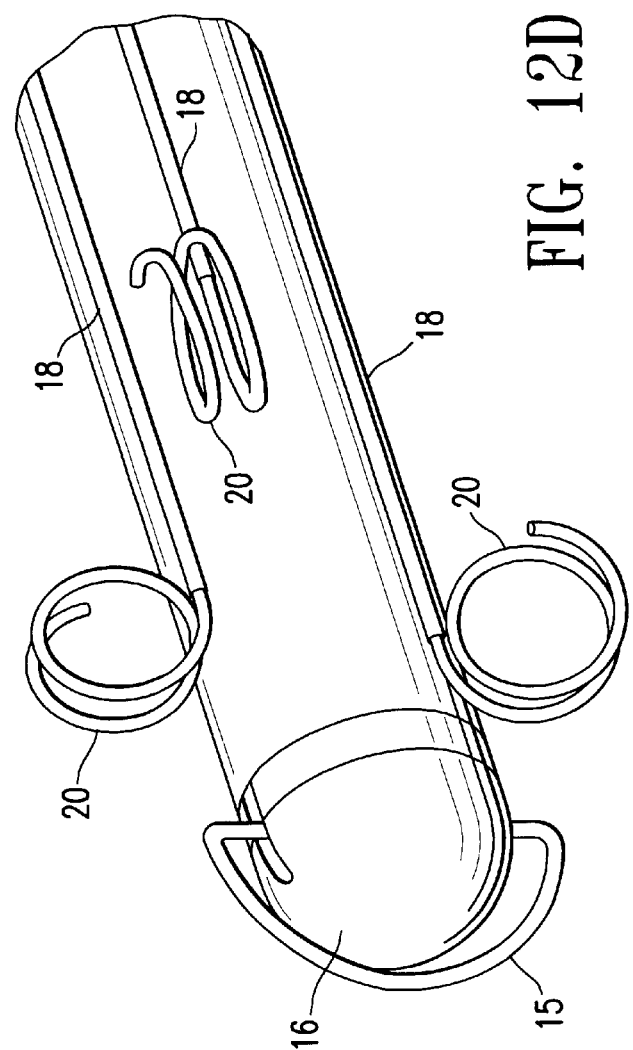
FIG. 12D is a perspective view of a portion of an elongated shaft of a device having anchoring elements deployed from positions proximal to the tip of the shaft embodying features of the invention.

Anchoring elements 20 may exit from anchoring element sheaths 18 for deployment into a patient's body from positions anywhere along the elongated shaft 13. For example, as illustrated in FIG. 12D, anchoring elements 20 may be deployed from positions proximal to the tip 16 of the shaft 13. In embodiments of the invention, anchoring elements 20 may deploy from positions of up to about 2 cm to 3 cm from the tip 16. In preferred embodiments, anchoring elements 20 deploying from positions proximal of tip 16 may deploy from positions up to about 0.5 cm to about 2 cm proximal of the tip 16. Note that some anchoring elements 20 may be deployed from sheaths 18 at a different distances from tip 16 than other anchoring elements 20.

FIG. 13 illustrates anchoring elements 20 and their sheaths 18 in various configurations. FIG. 14 illustrates different tip configurations: anchoring elements 20 may have flat or rounded tips 64, or may have barbs on their tips (66) as shown in FIG. 14B. It will be understood that anchoring elements 20 may have any of a variety of tip shapes and configurations, including but not limited to flat, rounded, beveled, pointed, barbed, or other configuration, and may be configured to assume tighter or looser coil configurations as well. Anchoring elements 20 may be made with any material having suitable spring-like properties. In preferred embodiments, anchoring elements 20 are made with superelastic nitinol wire configured to assume a coiled configuration upon release from enclosure within a sheath. The alignment of the anchoring elements 20 within anchoring element sheaths 18 is an important factor in obtaining a desired coil configuration upon deployment.

Anchoring elements 20, particularly anchoring elements 20 made with materials including super-elastic nitinol, may be configured and deployed so as to assume different coiled configurations upon exiting from anchoring element sheaths 18 depending upon the relative motions of the anchoring element 20, the sheath 18, and the tissue into which the anchoring element is deployed. In one deployment mode, advancing the anchoring elements 20 out of the anchoring element sheaths 18 into surrounding tissue lets the anchoring elements 20 assume their natural and restrained coil shapes. However, in an alternative deployment mode, the anchoring element sheaths 18 are pulled back while the anchoring elements 20 are left in a substantially static position. In this case, the tips 64 of the anchoring elements 20 do not move forward as they uncoil upon release from the restraint of the anchoring element sheaths 18, but instead remain relatively stationary or move backward, so that the final coil shapes of the anchoring elements 20 are substantially dictated by the composition of the surrounding tissue. The coil radius of an anchoring element 20 that is deployed into a region of harder or denser tissue will, in general, be smaller than the coil radius of an anchoring element 20 deployed into a region of softer or less dense tissue. In general, the wider the coil radius, the more the backward movement of the anchoring element tip 64 as an anchoring element 20 uncoils during retraction of an anchoring element sheath 18.

The following definitions are useful in describing the different anchoring element deployment configurations of devices and methods embodying features of the invention. An imaginary line following a path down the central axis of a helical coil is termed a "coil axis"; similarly, an imaginary line following a path down the central axis of a sheath is termed a "sheath axis." A coil axis and a sheath axis may be aligned in a substantially parallel alignment, or may not be similarly aligned. The alignment of a coil axis is termed to be "radial" to a sheath axis when the coil axis and the sheath axis are not substantially parallel, but instead, either meet at an angle, or a projection of the coil axis onto a plane including the sheath axis forms an angle with the sheath axis. A forward direction is defined as the direction along the sheath axis leading from the interior to the exterior of the sheath; a rearward direction is the direction along the sheath axis from the exterior to the interior of the sheath, and is opposite to a forward direction. Rearward movement is also termed "retraction."

When an anchoring element 20 made with material having suitable spring-like properties, such as super-elastic nitinol wire, is deployed into a tissue from a stationary anchoring element sheath 18, the anchoring element 20 will assume a coiled configuration with the coil axis substantially radial to the sheath axis. However, a different coil configuration is obtained when a super-elastic nitinol wire is deployed forward into a tissue from a sheath that is moving in a rearward direction. In this latter case, the coil, as it extends, will assume a configuration with the coil axis substantially parallel to the sheath axis. This property is useful for anchoring medical devices in a proper location within a patient's body.

FIG. 13A illustrates the configuration of an anchoring element 20 and an anchoring element sheath 18 embodying features of the invention following deployment of the anchoring element 20 with the sheath 18 held stationary. The anchoring element 20 assumes a radial configuration having a coil axis substantially perpendicular to the sheath axis. In embodiments of the invention, anchoring elements 20 may be configured to deploy from stationary sheaths into radial configurations having coil axis orientations at other angles with respect to the sheath axis as well. In FIG. 13B, an anchoring element 20 and an anchoring element sheath 18 are illustrated following forward deployment of the anchoring element 20 while the sheath 18 was moving in a rearward direction. In this case, the anchoring element 20 assumes a configuration with a coil axis substantially parallel to the sheath axis.

FIG. 13C illustrates an anchoring element 18 having a coil configuration produced by utilization of both methods of coiled wire deployment. The anchoring element 20 illustrated in FIG. 13C has a coiled portion having a coil axis oriented substantially perpendicularly with respect to the sheath axis, and a coil portion having a coil axis oriented substantially parallel to the sheath axis. This complex configuration may be produced by first deploying a super-elastic nitinol anchoring element 20 from a stationary anchoring element sheath 18, and then moving the anchoring element sheath 18 in a rearward direction while deploying the anchoring element 20 in a forward direction.

The anchoring element configurations illustrated in FIGS. 13A, 13B and 13C are effective to anchor a medical device in a desired location within a patient's body. At least one anchoring element is effective to anchor a medical device in a desired location within a patient's body. The use of at least two, or preferably at least three anchoring elements is believed to be more effective than the use of a single anchoring element. In particular, since lymph nodes are small, mobile, and difficult to identify and localize, use of an anchoring element or use of at least one, and preferably multiple anchoring elements, as disclosed herein, is effective to fix a medical device adjacent to a sentinel lymph node and to aid in the removal of sentinel lymph nodes, cancerous tissues, and of other tissues.

Figure 15A:
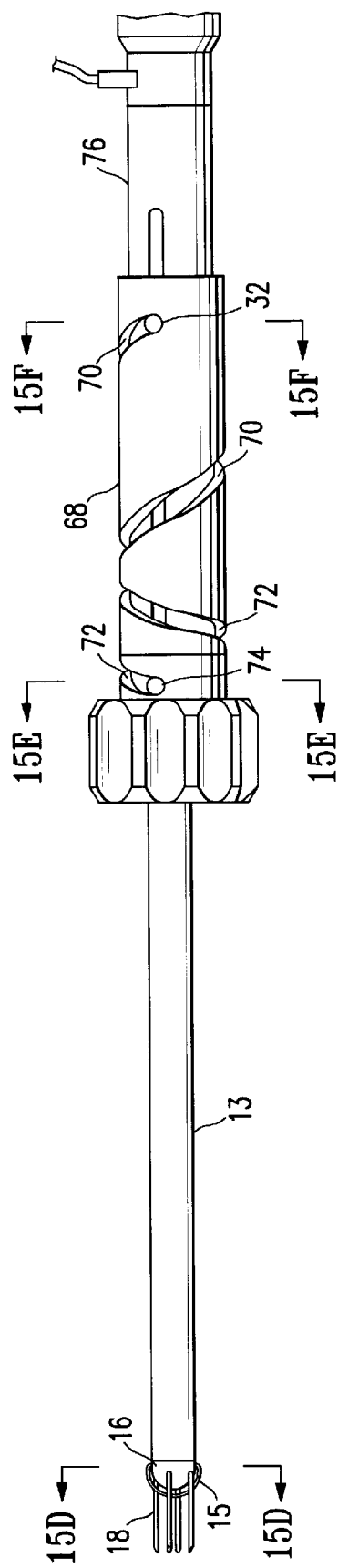
FIG. 15A illustrates a device embodying features of the invention having anchoring element sheaths shown in an extended position.
Figure 15B:
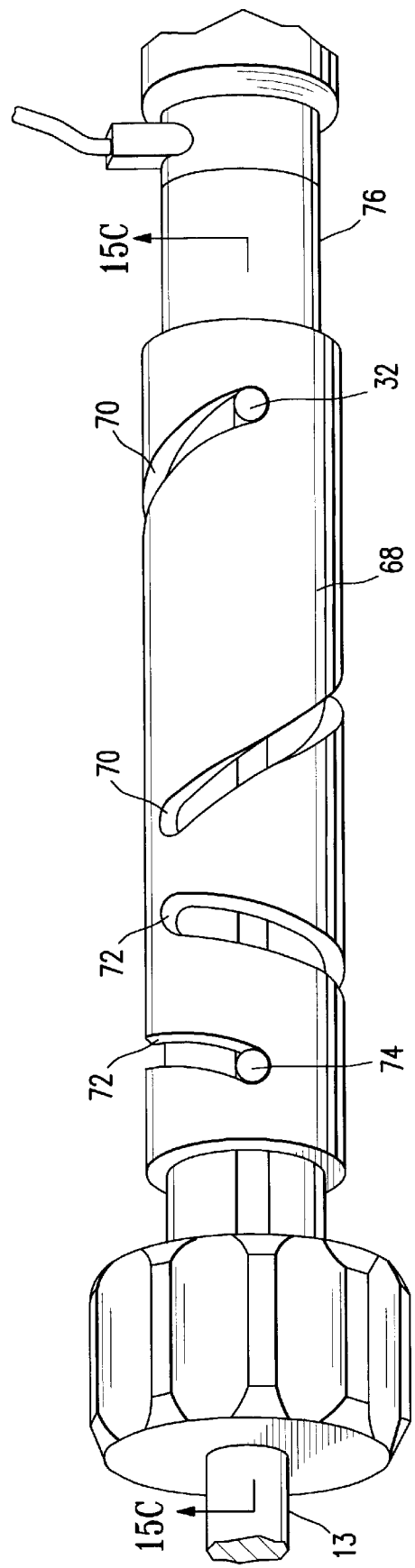
FIG. 15B is a perspective view of the handle portion of the device of FIG. 15A showing the configuration of extension tabs and extension slots when the anchoring element sheaths are in an extended position and anchoring elements retracted.
Figure 15C:
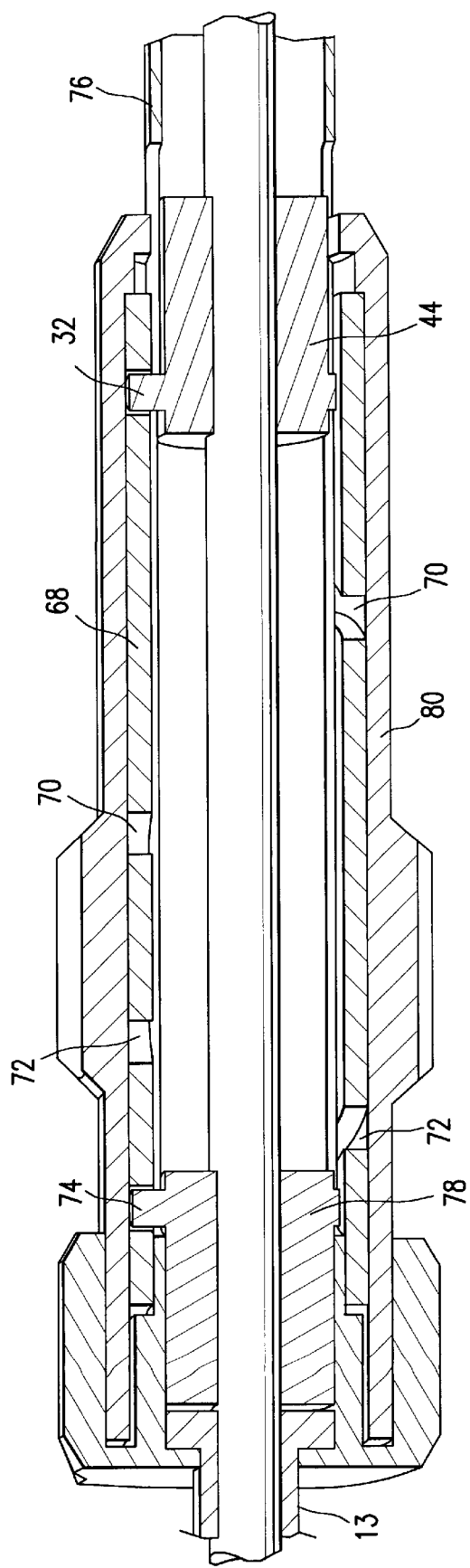
FIG. 15C is a longitudinal cross-sectional view of the handle portion of the device of FIG. 15A showing the configuration of extension tabs and extension slots when the anchoring element sheaths are in an extended position.

The anchoring element sheaths 18 may be configured for forward and rearward movement effective to deploy anchoring elements 20 into any desired configuration. FIGS. 15 and 16 illustrate an embodiment of a sentinel node accessing and anchoring device embodying features of the invention having sheaths and anchoring elements that may be deployed and retracted. FIG. 15A illustrates a device embodying features of the invention having anchoring element sheaths shown moved forward in an extended position. Anchoring elements 20 are contained within anchoring element sheaths 18. FIG. 15B illustrates the handle portion of the device of FIG. 15A to show the configuration of extension tabs and extension slots corresponding to the configuration of the anchoring element sheaths 18 and anchoring elements 20 shown in FIG. 15A. Slotted sleeve 68, having anchoring element slot 70 for controlling the configuration of anchoring elements 20 and sheath slot 72 for controlling the configuration of sheaths 18, is mounted on handle barrel 76. Push sleeve tab 32 and sheath push tab 74 are shown engaged within anchoring element slot 70 and sheath slot 72, respectively. FIG. 15C provides a cross-sectional view of the handle portion of the device of FIG. 15A and 15B, showing push sleeve tab 32 and push sleeve 44, and sheath push tab 74 and sheath push sleeve 78, engaged with slotted sleeve 68 within anchoring element slot 70 and sheath slot 72, respectively. Slotted sleeve 68 is shown here within rotating handle 80 which is a deployment actuator and also serves as a cover for slotted sleeve 68 in the embodiment illustrated in FIG. 15C. FIGS. 15D, 15E and 15F show transverse cross-sectional views of the device, taken along the lines 15D—15D, 15E—15E, and 15F—15F shown in FIG. 15A.

As illustrated in FIG. 13, forward deployment of anchoring elements while sheaths move rearward results in anchoring elements configured with coil axes substantially parallel to the sheath axes. Thus, in order that anchoring elements 20 will assume the configurations shown in FIG. 16A, anchoring elements 20 are deployed forward, and sheaths 18 moved rearward, during deployment of the anchoring elements 20 from the device shown in FIG. 15A. The configurations of the anchoring elements 20 are shown in greater detail in FIG. 16B. As is also more readily seen in FIG. 16B, sheaths 18 have been fully retracted within tip 16 and shaft 13 into anchoring element support sleeve 46. Support sleeve 46 and anchoring element sheath 18 together form a telescoping tubular sleeve configured to extend and retract while retaining an anchoring element 20 within a restraining enclosure effective to avoid buckling of the enclosed anchoring element 20.

Figure 16A:
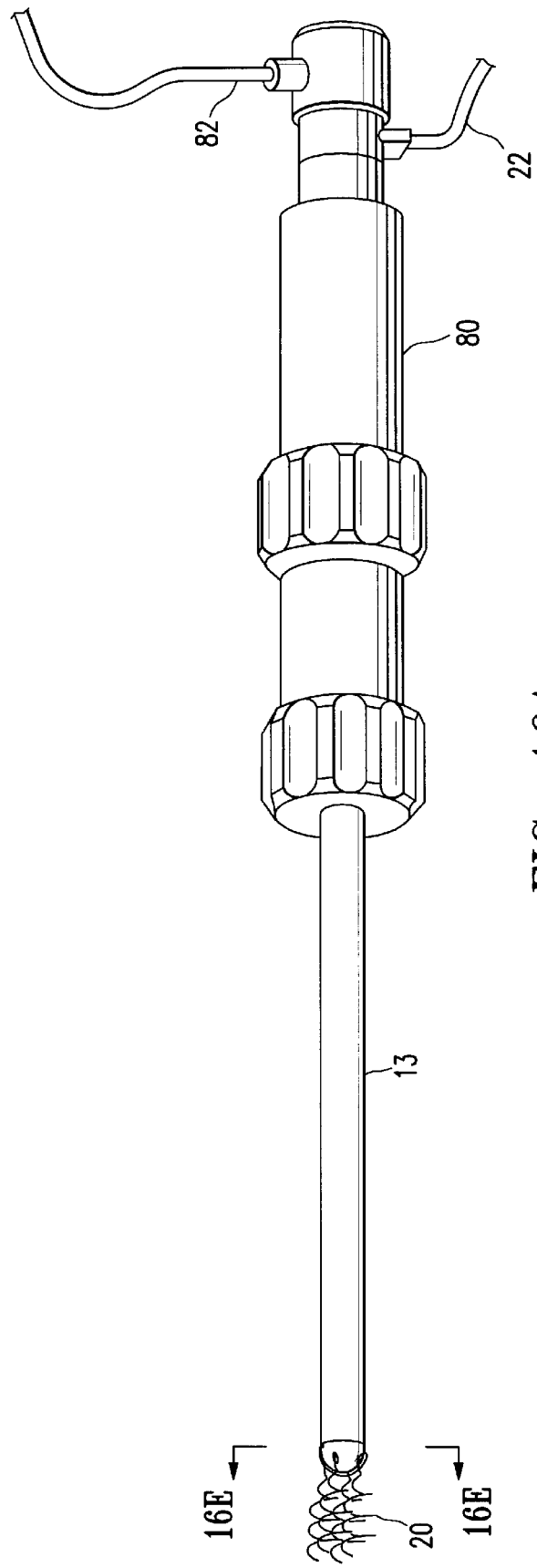
FIG. 16A illustrates a device embodying features of the invention having anchoring element sheaths retracted and anchoring elements deployed.
Figure 16B:
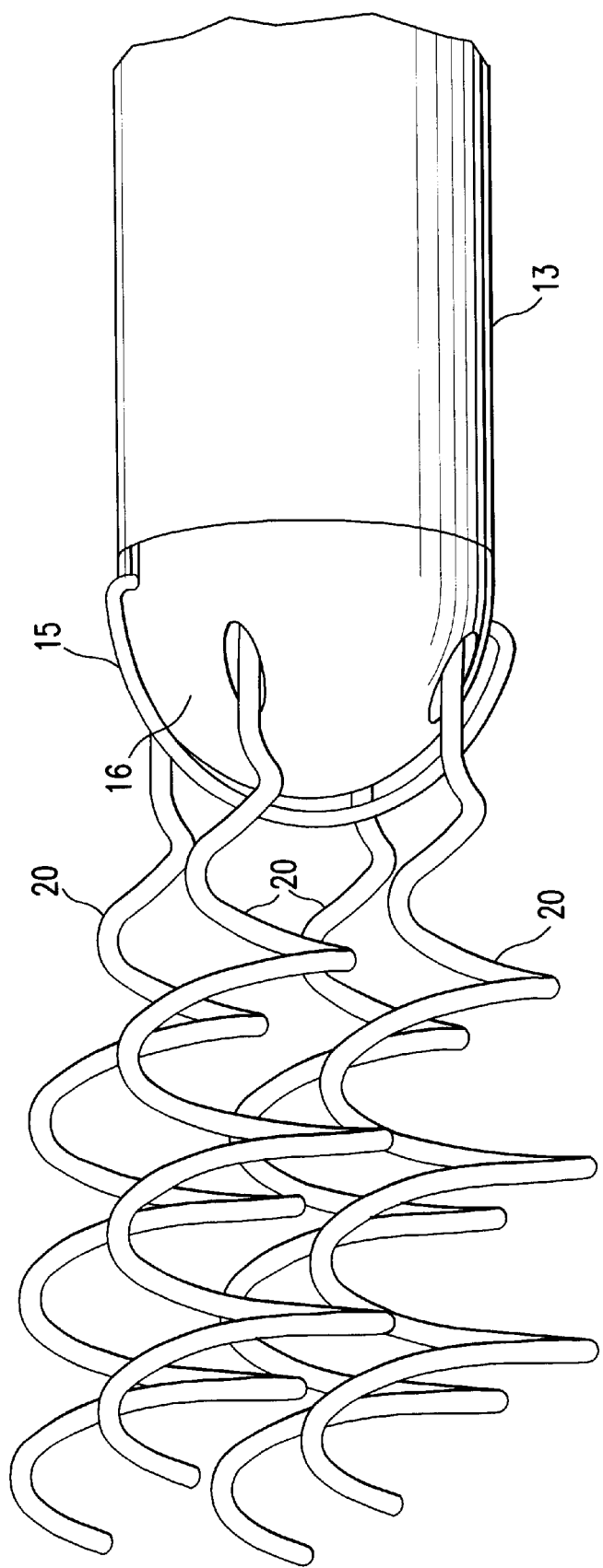
FIG. 16B illustrates a distal portion of the device of FIG. 16A showing deployed anchoring elements.
Figure 16C:
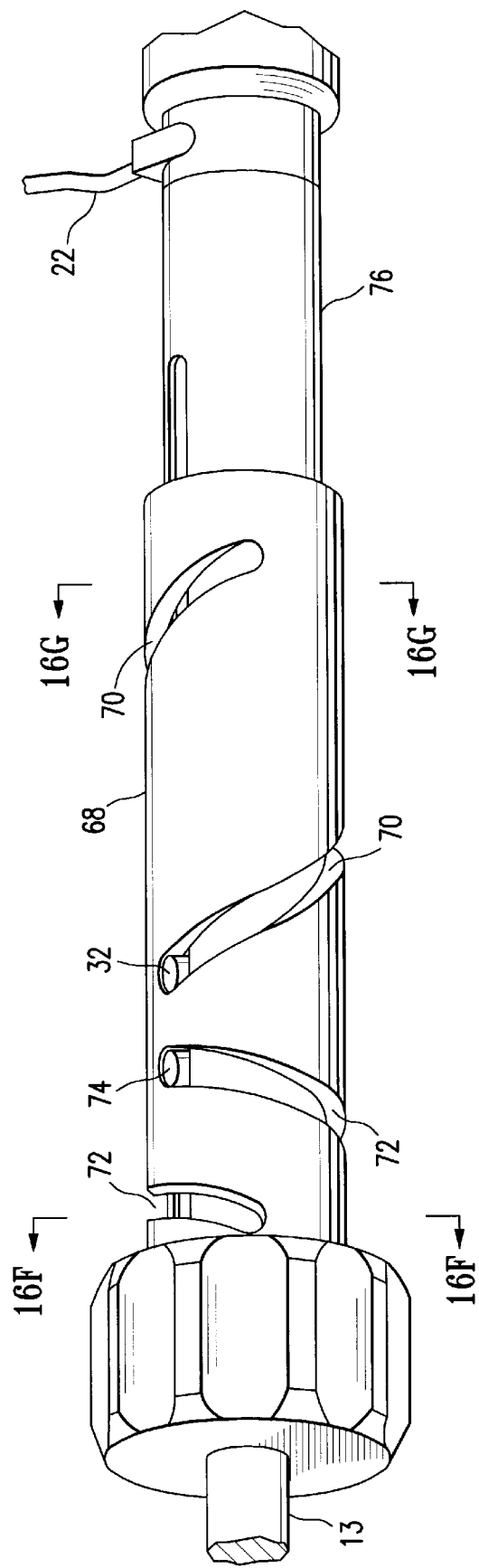
FIG. 16C is a perspective view of the handle portion of the device of FIG. 16A showing the configuration of extension tabs and extension slots when the anchoring elements are deployed and the sheaths retracted.
Figure 16D:
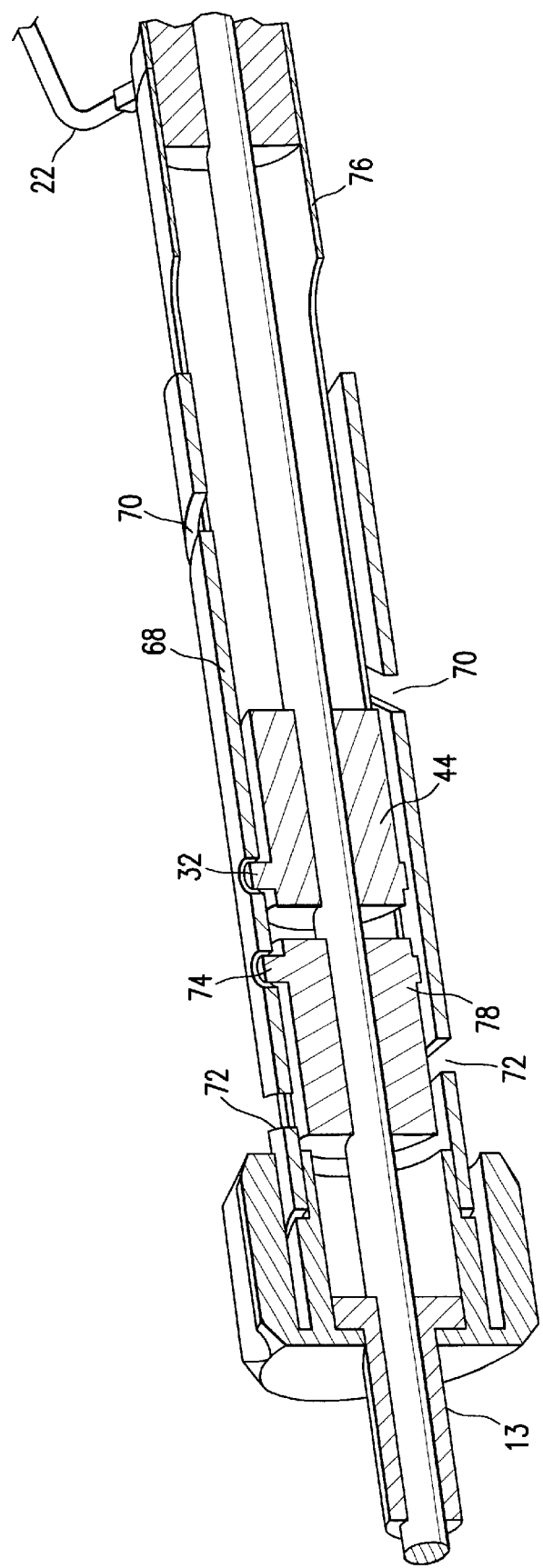
FIG. 16D is a longitudinal cross-sectional view of the handle portion of the device of FIG. 16A showing the configuration of extension tabs and extension slots when the anchoring elements are deployed and the sheaths retracted.
Figure 16E:
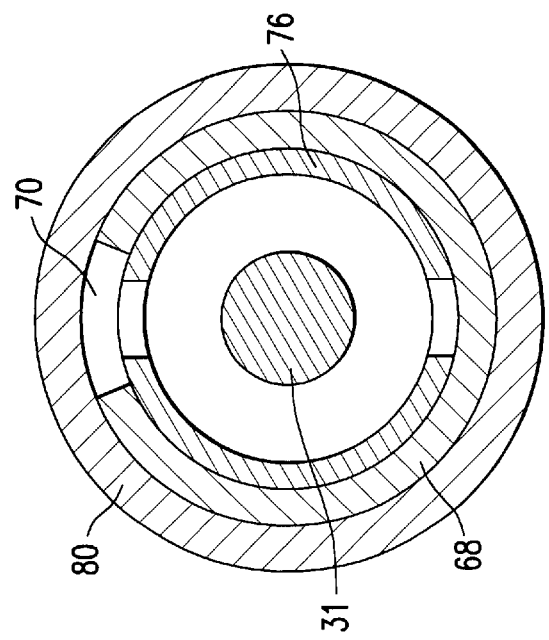
FIG. 16E is a transverse cross-sectional view taken along line 16E—16E of the device of FIG. 16A.
Figure 16F:
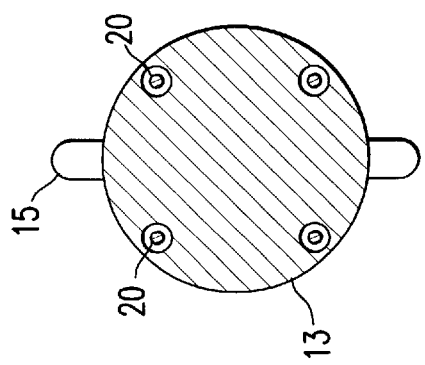
FIG. 16F is a transverse cross-sectional view taken along line 16F—16F shown in FIG. 16C.
Figure 16F:
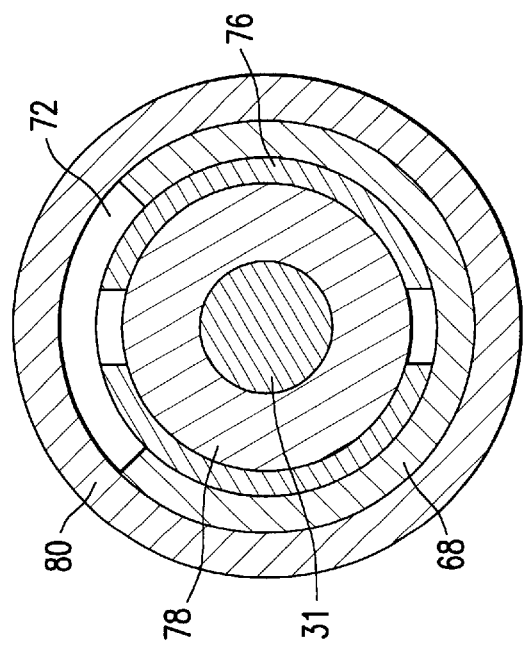

FIG. 16C shows the handle portion of the device of FIG. 15 and 16. With sheaths 18 retracted and anchoring elements 20 deployed, sheath tab 74 and push sleeve tab 32 are located in the positions near to each as shown in FIGS. 16C and 16D. FIGS. 16E, 16F, and 16G show transverse cross-sectional views of the device of FIG. 16A, taken along the lines 16E—16E, 16F—16F, and 16G—16G in the figures. Also shown in FIGS. 16A–16D are RF connection 22 and electrical connector 82 for the radiation energy detector 30.

Sentinel node accessing and anchoring devices embodying features of the invention find use in the detection, marking and removal of lymph nodes and other tissues that may harbor metastatic cancer cells. A patient, such as one having a cancerous lesion, may be injected with radiation-emitting material at the primary lesion site. Radioactive materials may be bio-compatible fluids containing, e.g., Technetium 99, Indium 111, Iodine 123 or Iodine 125, which emit gamma radiation, or may be bio-compatible fluids containing materials emitting alpha-radiation or beta-radiation. Detection of radiation by radiation energy detector probe 30 at a location other than the injection site indicates that migration of the radioactive material has occurred, typically via the lymphatic system.

Identification and removal of sentinel lymph nodes is an important part of cancer treatment, particularly the treatment of breast cancer. By correctly timing the observation of the radiation energy signals coming from the patient's body after injection of radioactive material, it is possible to locate and identify the sentinel lymph nodes corresponding to a lesion site. Alternatively, lack of gamma radiation emission from a lymph node, at a time after injection sufficient to allow lymph drainage into a sentinel lymph node, indicates that the node is not in communication with the cancerous lesion and so is not at high risk of harboring metastatic cancer cells. The lymph nodes which correspond to the breast and surrounding areas are typically located in the armpit of the patient, connected to breast tissue by a series of lymph ducts.

As described in copending, co-owned U.S. patent application Ser. No. 09/727,112 "Sentinel Node Location and Biopsy" to Burbank and Lubock, monitoring of a patient following injection of radioactive material may be accomplished by hand held radiation detector, gamma camera, or other radiation detector. Detection of an accumulation of radioactive material at a time after the injected radioactive material has migrated through the lymph ducts to the sentinel lymph nodes but prior to dispersion of the radioactive material to nodes surrounding the sentinel nodes indicates that a sentinel lymph node has been located. "Hot" sentinel lymph nodes are clearly distinguishable from surrounding non-radioactive lymph nodes using radiation energy detectors from outside the patient's body, sufficient to indicate an approximate position of sentinel lymph nodes in a non-invasive manner. A mark may be made on the skin of the patient to identify the approximate location of the sentinel lymph node identified in this way by an external radiation detector such as a hand-held radiation detector or gamma camera.

However, knowledge of only the approximate location of a sentinel lymph node is insufficient for its accurate and complete removal. Use of a sentinel node accessing and anchoring device 11 embodying features of the invention allows location of the sentinel lymph nodes with greater precision, and allows their precise marking for their accurate and complete removal. Thus, the invention provides an improved method for accessing and anchoring a sentinel lymph node corresponding to a lesion site within a patient's body that makes use of the devices and systems of the invention to access a sentinel lymph node and to anchor the device in or adjacent the sentinel lymph node.

An improved method for accessing and anchoring a sentinel lymph node corresponding to a lesion site within a patient's body includes the step of locating the approximate position of at least one sentinel lymph node by detecting radiation accumulated within a lymph node with a radiation detector. For example, the radiation detector may be a radiation energy detector probe 30 having an elongated portion 31 configured to slidably fit within shaft 13. Then, the device 11 may be used to access the sentinel lymph node by activating cutting wire 15 to ablate tissue while passing shaft 13 into the patient's body until the distal end 14 of the shaft 13 or the tip 16 is disposed adjacent the sentinel lymph node. Anchoring elements 20 may then be extended into the patient's body tissue to anchor the device 11 into the sentinel lymph node or into tissue adjacent the sentinel lymph node. The extension of the anchoring elements is effective to secure the distal end 14 of shaft 13 or the tip 16 to the sentinel lymph node or adjacent to the sentinel lymph node.

The anchoring elements 20 may be extended radially or longitudinally. Anchoring elements 20 may assume a curved or coiled configuration when extended, as shown in FIGS. 1B, 7–11, 12A, 13, 14, and 16A and B. Once the device 11 is secured to or adjacent a sentinel lymph node by anchoring elements 20, the patient can be transferred to a surgical suite and the lymph node surgically removed, with the device 11 attached and serving as a locating device.

A sentinel node accessing and anchoring device 11 may be introduced into a patient's body at a location corresponding to the approximate location of a sentinel lymph node identified by external radiation detectors. Ultrasonic imaging can be used while the device 11 is being inserted to aid its guidance to a desired location and to help avoid the large arteries and nerves that are generally located in the same area as the axillary lymph nodes of a patient.

Cutting wire 15 may be spaced distally from tip 16, as illustrated in the figures, or may be partly or completely in contact with tip 16. Cutting wire 15 readily cuts through tissue upon activation with RF power from RF power source 24, allowing insertion of tip 16 and shaft 13 into a patient. When cutting wire 15 is activated with RF energy and applied to tissue, tissue is ablated along the length of the cutting wire 15 and displaced by tip 16 of device 11 as it is advanced through the tissue. Because RF tissue ablation frequently interferes with ultrasonic imaging and the like, it may be desirable to use a system for reduction of such interference such as is taught by copending U.S. patent application Ser. No. 09/527,868, by Dabney et al., filed Mar. 17, 2000, which is hereby incorporated by reference herein in its entirety.

The RF power source 24 for the cutting wire 15 can be any of a variety of standard electrosurgical units generating radiofrequency energy in a range of about 300 to about 6,000 kHz, specifically, about 350 to about 1,000 kHz. Power output for the RF power source 24 can be about 25 to about 150 watts, preferably about 75 to about 125 watts. The cutting wire 15 can be made of a variety of materials, including stainless steel, tungsten, nitinol and the like.

Cutting wire 15 may have a cross section that is round, rectangular, oval or any other suitable configuration and generally has a transverse dimension of about 0.001 to about 0.020 inch, specifically about 0.006 to about 0.015 inch. As illustrated in FIG. 1 and other figures, the cutting wire is spaced distally from tip 16, although in embodiments of the invention cutting wire 15 is not spaced distally from the tip 16.

The cutting element at the tip of devices embodying features of the invention may have a sharp cutting surface, point or edge for use without electrical power. In preferred embodiments, the cutting element is an electrode, such as cutting wire 15, configured for use with RF power to cut through tissue. In addition to the application of RF energy to cutting wire 15 as described, in embodiments of the invention anchoring elements 20 may receive RF energy from RF power source 24 or other RF power source in order to apply RF power to tissue to aid their deployment. Thus, RF energy may be applied to the cutting wire 15 to effect insertion and movement of tip 14 and shaft 13 of devices of the invention, and may also be applied to anchoring elements 20 during their deployment to aid in their advancement through tissue. In embodiments of the invention, anchoring elements 20 may be insulated along their lengths except for at the tips 64.

Shaft 13 and tip 16 may be made from any bio-compatible materials, such as bio-compatible polymers, ceramics, composites, or metals (the metal preferably having an electrically insulated outer surface or coating). Preferably, shaft 13 is made from a disposable polymer sleeve configured to fit over the elongated portion 31 of radiation detector probe 30. Tip 16 is preferably formed, at least in part, from high density polyethylene (HDPE).

The invention also provides systems for accessing and anchoring a sentinel node within a patient, including a device 11, having a shaft 13, a tissue cutting member such as cutting wire 15, a radiation energy detector probe 30, the device 11 having at least one anchoring element 20 having a retracted and having an extended configuration, and a rotating handle 80 configured to deploy an anchoring element 20 from the retracted configuration to the extended configuration. In embodiments of the invention, rotating handle 80, which serves as a deployment actuator, may be configured to both extend the anchoring elements 20 and to activate the anchor elements 20 with RF energy. In addition, the system may include a housing, an inner conductor, a main shaft disposed within an inner lumen of the inner conductor, an actuator coupled to the inner conductor for extending the anchoring elements 20 and an RF energy source switchably coupled to the inner conductor.

While particular forms of the invention have been illustrated and described, it should be apparent that various modifications can be made without departing from the spirit and scope of the invention. Accordingly, it is not intended that the invention be limited, except as by the appended claims.

What is claimed is:

1. A tissue accessing and anchoring device, comprising:
   a. an elongated shaft having a distal end and a proximal end;
   b. a tissue cutting member at the distal end of the shaft to provide access to a target site;
   c. at least one movable sheath having a distal end at or near the distal end of the shaft, a port in the distal end of the sheath and an inner bore leading to and in fluid communication with the port in the distal end; and
   d. at least one anchoring element which is slidably disposed within the inner bore of the sheath and positioned at or near the distal end of the shaft, which is configured to move within said inner bore, to extend out of the port in the distal end of the movable sheath, beyond the distal end of the shaft and which is configured to extend into tissue at the target site to thereby anchor the device.

2. The accessing and anchoring device of claim 1 wherein the extended anchoring element forms a curved structure as it extends out the port in the distal end of the sheath.

3. The accessing and anchoring device of claim 2 wherein the curved structure comprises a helical coil.

4. The accessing and anchoring device of claim 2 wherein the curved structure of the anchoring element extends through at least 180°.

5. The accessing and anchoring device of claim 2 wherein the curved structure of the anchoring element extends through at least 360°.

6. The accessing and anchoring device of claim 2 wherein the curved structure of the anchoring element extends through at least 540°.

7. The accessing and anchoring device of claim 1 wherein the anchoring element extends radially from the shaft.

8. The accessing and anchoring device of claim 7 wherein the anchoring element comprises a helical coil.

9. The accessing and anchoring device of claim 1 wherein the anchoring element extends longitudinally.

10. The accessing and anchoring device of claim 9 wherein the anchoring element comprises a helical coil.

11. The accessing and anchoring device of claim 1 wherein the elongated shaft has an inner lumen extending to a location at or near the distal end of the shaft.

12. The accessing device of claim 11 wherein a radiation detector is provided on a distal extremity of an elongated member slidably disposed within the inner lumen of the elongated shaft.

13. The accessing and anchoring device of claim 1 wherein the tissue cutting member on the distal end of the shaft is an electrode.

14. The accessing and anchoring device of claim 13 wherein the electrode has an electrically active surface.

15. The accessing and anchoring device of claim 14 wherein the electrically active surface has a sharp edge.

16. The accessing and anchoring device of claim 13 wherein the tissue cutting electrode is configured to be electrically connected to an RF energy source.

17. The accessing and anchoring device of claim 13 wherein an electrosurgical cutting edge of the cutting member is spaced from the distal end of the shaft.

18. The accessing and anchoring device of claim 13 wherein an electrosurgical cutting edge has an arcuate shape.

19. The accessing and anchoring device of claim 1, having at least two radially extending anchoring elements.

20. The accessing and anchoring device of claim 1, having at least three radially extending anchoring elements.

21. The accessing and anchoring device of claim 19 wherein the radially extending anchoring elements extend along a substantial length of the shaft.

22. The accessing and anchoring device of claim 21 wherein the substantial length of the elongate shaft through which the anchoring elements extend has an oblong transverse cross section.

23. A tissue accessing and anchoring device, comprising:
   a. an elongated shaft having a distal end, a proximal end and at least a distal portion having an oblong transverse cross section along the length thereof;
   b. a tissue cuffing member at or beyond the distal end of the shaft to provide access to a target site;
   c. a plurality of movable sheaths each having a distal end at or near the distal end of the shaft, a port in the distal end of the sheath and an inner bore leading to and in fluid communication with the port in the distal end; and d. a plurality of elongated anchoring elements, each of which is configured to move within the inner bore of a sheath, to extend from the port in the distal end of the movable sheath along the portion of the elongated shaft having an oblong transverse cross section, to extend beyond the distal end of the shaft and which is configured to extend into tissue at the target site to thereby anchor the device.

24. The tissue accessing and anchoring device of claim 23 wherein the plurality of elongated anchoring elements extending along said length of the shaft having an oblong transverse cross section are parallel and extend along a long dimension of the oblong transverse cross section.

25. A node accessing and anchoring device comprising:

an elongated shaft having a longitudinal axis, a distal end and a proximal end;

a tissue cutting member at the distal end of the shaft;

a movable sheath having an inner bore;

at least one radially extending anchoring element which is configured to extend into tissue at a target site and which is disposed within said inner bore of said movable sheath at or near the distal end of the shaft, the at least one radially extending anchoring element having a retracted configuration and a deployed configuration extending from the distal end of the shaft; and a deployment actuator disposed proximal of the distal end of the elongate shaft and configured to deploy the radially extending anchoring element from a retracted configuration to an extended configuration.

26. The node accessing and anchoring device of claim 25, wherein the anchoring element forms a curved structure as it extends radially.

* * * * *